US012674194B2

(12) United States Patent
Witters et al.

(10) Patent No.: US 12,674,194 B2
(45) **Date of Patent: *Jul. 7, 2026**

(54) IN SITU NUCLEIC ACID AMPLIFICATION

(71) Applicant: Singular Genomics Systems, Inc., La Jolla, CA (US)

(72) Inventors: Daan Witters, San Diego, CA (US); Allen Lipson, San Diego, CA (US); Eli N. Glezer, Del Mar, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/704,895

(22) Filed: Mar. 25, 2022

(65) Prior Publication Data

US 2022/0235410 A1 Jul. 28, 2022

Related U.S. Application Data

(63) Continuation of application No. PCT/US2021/031517, filed on May 10, 2021.

(60) Provisional application No. 63/023,752, filed on May 12, 2020.

(51) Int. Cl.

*C12Q 1/68* (2018.01)
*C12Q 1/6806* (2018.01)
*C12Q 1/6844* (2018.01)

(52) U.S. Cl.

CPC ......... *C12Q 1/6844* (2013.01); *C12Q 1/6806* (2013.01)

(58) Field of Classification Search

None

See application file for complete search history.

(56) References Cited

U.S. PATENT DOCUMENTS 4,318,846 A 3/1982 Khanna et al.
5,034,506 A 7/1991 Summerton et al.
5,066,580 A 11/1991 Lee
5,188,934 A 2/1993 Menchen et al.
5,235,033 A 8/1993 Summerton et al.
5,366,860 A 11/1994 Bergot et al.
5,426,180 A 6/1995 Kool
5,599,675 A 2/1997 Brenner
5,641,658 A 6/1997 Adams et al.
5,688,648 A 11/1997 Mathies et al.
5,750,341 A 5/1998 Macevicz
5,763,594 A 6/1998 Hiatt et al.
5,800,996 A 9/1998 Lee et al.
5,808,045 A 9/1998 Hiatt et al.
5,847,162 A 12/1998 Lee et al.
5,872,244 A 2/1999 Hiatt et al.
6,210,891 B1 4/2001 Nyren et al.
6,232,465 B1 5/2001 Hiatt et al.
6,258,568 B1 7/2001 Nyren
6,274,320 B1 8/2001 Rothberg et al.
6,664,079 B2 12/2003 Ju et al.
7,057,026 B2 6/2006 Barnes et al.
7,115,400 B1 10/2006 Adessi et al.
7,435,572 B2 10/2008 Bitinaite
7,541,444 B2 6/2009 Milton et al.
7,790,418 B2 9/2010 Mayer
8,003,354 B2 8/2011 Shen et al.
8,178,360 B2 5/2012 Barnes et al.
10,738,072 B1 8/2020 Graham et al.
11,486,004 B2 11/2022 Witters et al.
12,139,759 B2 11/2024 Witters et al.
2008/0009420 A1 1/2008 Schroth et al.
2009/0118128 A1 5/2009 Liu et al.
2011/0065151 A1 3/2011 Kumar et al.
2011/0207135 A1* 8/2011 Faham ............... C12N 15/1072 435/6.11
2012/0238738 A1 9/2012 Hendrickson
2013/0012399 A1 1/2013 Myers et al.
2014/0032275 A1 1/2014 Kalb et al.
2015/0017635 A1 1/2015 Myllykangas et al.
2015/0376692 A1* 12/2015 Esfandyarpour .... G01N 27/745 506/38
2016/0116384 A1 4/2016 Chen et al.
2016/0272954 A1* 9/2016 Li ........................ C12Q 1/6855
2017/0016063 A1* 1/2017 McGall .............. C12N 15/1065
2017/0067097 A1* 3/2017 Metzker ............... C12Q 1/6855
2017/0159136 A1 6/2017 Church et al.
2018/0002735 A1* 1/2018 Drmanac ............. C12Q 1/6809
2018/0100192 A1* 4/2018 Boutell .................. C12N 15/10
2018/0105871 A1* 4/2018 Korfhage ............. C12Q 1/6837
2018/0258472 A1 9/2018 Glezer
2018/0274024 A1 9/2018 Ju et al.
2018/0320226 A1* 11/2018 Church .................. C12N 15/11

(Continued)

FOREIGN PATENT DOCUMENTS

WO WO 1989/010977 A1 11/1989
WO WO1996007669 A1 3/1996

(Continued)

OTHER PUBLICATIONS

Bains, W. et al. (Dec. 7, 1988). "A novel method for nucleic acid sequence determination," J Theor Biol 135(3):303-307.

Beattie, W. et al. (1995) "Hybridization of DNA targets to glass-tethered oligonucleotide probes." Molecular biotechnology 4(3): 213-225.

Bentley, D.R. et al. (Nov. 6, 2008). "Accurate whole human genome sequencing using reversible terminator chemistry," Nature 456(7218):53-59.

Bergen, K. et al. (Jun. 17, 2013, e-published Jun. 3, 2013). "Structures of KOD and 9°N DNA polymerases complexed with primer template duplex," Chembiochem 14(9):1058-1062.

Chen, F. et al. (2015) "Expansion microscopy." Science 347(6221): 543-548.

(Continued)

*Primary Examiner* — Suryaprabha Chunduru

(74) *Attorney, Agent, or Firm* — Mintz, Levin, Cohn, Ferris, Glovsky and Popeo, P.C; Zachary L. Terranova

(57) ABSTRACT

Disclosed herein, inter alia, are novel methods pertaining to nucleic acid amplification and sequencing. Compositions for use in and produced by such methods are also provided.

23 Claims, 13 Drawing Sheets

Specification includes a Sequence Listing.

(56) References Cited

U.S. PATENT DOCUMENTS

| | | | | |
|---|---|---|---|---|
| 2019/0032128 | A1* | 1/2019 | Chen | C12Q 1/6809 |
| 2019/0127792 | A1* | 5/2019 | Lebofsky | C12Q 1/6855 |
| 2019/0352327 | A1 | 11/2019 | Wu et al. | |
| 2021/0032618 | A1 | 2/2021 | Driscoll et al. | |
| 2021/0189460 | A1 | 6/2021 | Hosono et al. | |
| 2022/0243268 | A1 | 8/2022 | Witters et al. | |
| 2023/0095409 | A1 | 3/2023 | Witters et al. | |
| 2024/0271207 | A1 | 8/2024 | Witters et al. | |
| 2025/0027151 | A1 | 1/2025 | Witters et al. | |

FOREIGN PATENT DOCUMENTS

| | | | | |
|---|---|---|---|---|
| WO | 9718328 A1 | 5/1997 | | |
| WO | WO 2004/018497 A2 | 3/2004 | | |
| WO | WO 2004/018497 A3 | 3/2004 | | |
| WO | WO-2004067726 A2 | 8/2004 | * | C12Q 1/6848 |
| WO | 2004067726 A3 | 12/2005 | | |
| WO | WO-2008/070352 A2 | 6/2008 | | |
| WO | WO-2014030066 A2 | 2/2014 | * | C12Q 1/6809 |
| WO | 2014030066 A3 | 5/2014 | | |
| WO | 2016156845 A1 | 10/2016 | | |
| WO | WO-2016/170182 A1 | 10/2016 | | |
| WO | WO 2017/205336 A1 | 11/2017 | | |
| WO | WO 2018/148723 A1 | 8/2018 | | |
| WO | WO-2019/086531 A1 | 5/2019 | | |
| WO | 2019209946 A1 | 10/2019 | | |
| WO | WO-2019/222264 A1 | 11/2019 | | |
| WO | WO 2020/056044 A1 | 3/2020 | | |
| WO | 2021231263 A2 | 11/2021 | | |
| WO | 2021231263 A3 | 12/2021 | | |
| WO | 2022015600 A2 | 1/2022 | | |
| WO | WO-2022/015913 A1 | 1/2022 | | |

OTHER PUBLICATIONS

Chen, K. H. et al. (2015) RNA imaging. Spatially resolved, highly multiplexed RNA profiling in single cells. Science. 348: aaa6090.

Christian, AT et al. (2001) Proc Natl Acad Sci USA. 98(25):14238-14243.

Dirks, RM, and Pierce, N. (2004) "Triggered amplification by hybridization chain reaction." Proceedings of the National Academy of Sciences 101(43): 15275-15278.

Dolinnaya, N. et al. (Nov. 25, 1993) "Oligonucleotide circularization by template-directed chemical ligation," Nucleic Acids Research, vol. 21:23, 5403-5407.

Drmanac, S. et al. (Jan. 1998). "Accurate sequencing by hybridization for DNA diagnostics and individual genomics," Nat Biotechnol 16(1):54-58.

Fan, T. et al. (2018) Cancer science. 109(9):2827-2906, https://doi.org/10.1111/cas.13725.

Feeney, R. et al. (Apr. 1, 1982) Modification of Proteins; Advances in Chemistry, vol. 198, American Chemical Society.

Fodor, S.P. et al. (Feb. 15, 1991). "Light-directed, spatially addressable parallel chemical synthesis," Science 251(4995):767-773.

Fuller, C.W. et al. (May 10, 2016, e-published Apr. 18, 2016). PNAS USA 113(19):5233-5238.

Guo, J. et al. (Jul. 8, 2008, e-published Jun. 30, 2008). PNAS USA 105(27):9145-9150.

International Search Report mailed on Nov. 10, 2021, for PCT Application No. PCT/US2021/31517, filed May 10, 2021, 16 pages.

Kershaw, CJ., and O'Keefe, RT. (2012) "Splint ligation of RNA with T4 DNA ligase." Methods Mol Biol. 941: 257-269. 10.1007/978-1-62703-113-4_19.

Kumar, S. et al. (2012, e-published Sep. 21, 2012). "PEG-labeled nucleotides and nanopore detection for single molecule DNA sequencing by synthesis," Sci Rep 2:684.

Lage, J. et al., (Mar. 2003) Genome Research 13(2):294-307.

Larsson, C. et al. (2010) "In situ detection and genotyping of individual mRNA molecules." Nature methods 7(5): 395-397.

Lee, JH et al. (2015) "Fluorescent in situ sequencing (FISSEQ) of RNA for gene expression profiling in intact cells and tissues." Nature protocols 10(3): 442-458.

Lizardi, P.M. et al. (Jul. 1998). "Mutation detection and single-molecule counting using isothermal rolling-circle amplification," Nat. Genet. 19(3):225-232.

Nilsson, M. et al. (1994) "Padlock Probes: Circularizing Oligonucleotides for Localized DNA Detection" Science, vol. 265 Issue 5181:2085-2088.

Ronaghi, M. (Jan. 2001). "Pyrosequencing sheds light on DNA sequencing," Genome Res 11(1):3-11.

Ronaghi, M. et al. (1996) "Real-time DNA sequencing using detection of pyrophosphate release." Analytical biochemistry 242(1): 84-89.

Ronaghi, M. et al. (Jul. 17, 1998). "A sequencing method based on real-time pyrophosphate," Science 281(5375):363-365.

Rubin, E. et al. "Convergent DNA synthesis: a non-enzymatic dimerization approach to circular oligodeoxynucleotides." Nucleic acids research 23.17 (1995): 3547-3553.

Sansone, A. (2019) "Spatial transcriptomics levels up." Nature Methods 16(6): 458-458.

Shendure, J. et al. (2005) "Accurate multiplex polony sequencing of an evolved bacterial genome," Science 309(5741):1728-1732.

Southworth, MW et al.(1996) PNAS (93)11: 5281-5285, 8281-8285.

Wang, G. et al. (2018). "Multiplexed imaging of high-density libraries of RNAs with MERFISH and expansion microscopy." Scientific reports 8:4847.

Wang, X., et al. "Three-dimensional intact-tissue sequencing of single-cell transcriptional states." Science 361.6400 (2018): eaat5691.

International Search report mailed on Dec. 30, 2021, for PCT application PCT/US2021/41139, filed Jul. 9, 2021, 5 pages.

Written Opinion mailed on Dec. 30, 2021, for PCT application PCT/US2021/41139, filed Jul. 9, 2021, 13 pages.

Extended European Search Report mailed on May 21, 2024 for EP Patent Application No. 21803916.2, 8 pages.

Rakszewska, A. et al. (Jun. 1, 2016, e-published Apr. 14, 2016). "Quantitative Single-Cell mRNA Analysis in Hydrogel Beads," Angewandte Chemie 128(23): 6810-6813.

Cai, Matthew Zhipong (2019) "Spatial mapping of single cells in human cerebral cortex using DARTFISH: A highly multiplexed method for in situ quantification of targeted RNA transcripts", UC San Diego, 108 pages.

Cremer et al. (2008) "Multicolor 3D Fluorescence in Situ Hybridization for Imaging Interphase Chromosomes", R. Hancock (ed.) The Nucleus: vol. 1: Nuclei and Subnuclear Components, 1:205-239.

Korfhage et al. (May 12, 2017) "Clonal Rolling Circle Amplification for on-chip DNA Cluster Generation", Biology Methods and Protocols, 2(1):1-10.

Lee et al. (Nov. 27, 2007) "Functionalization of Poly(oligo(ethylene glycol) methacrylate) Films on Gold and Si/SiO2 for Immobilization of Proteins and Cells: SPR and QCM Studies", Biomacromolecules, 8(12):3922-3929.

Mag et al. (Nov. 24, 1992) "Synthesis and Selective Cleavage of an Oligodeoxynucleotide Containing a Bridged Non-Chiral Internucleotide 3'-phosphoramidate Linkage", Tetrahedron Letters, 33(48):7319-7322.

Rattray et al. (2003) "Error-prone DNA polymerases: when making a mistake is the only way to get ahead", Annual Review of Genetics, 37:31-66.

Walker et al. (Oct. 1, 1988,) "Photolabile 1-(2-Nitrophenyl)Ethyl Phosphate Esters of Adenine Nucleotide Analogs. Synthesis and Mechanism of Photolysis", Journal of the American Chemical Society, 110(21):7170-7177.

* cited by examiner

SEQUENCE LISTING

```
<160> NUMBER OF SEQ ID NOS: 8

<210> SEQ ID NO 1
<211> LENGTH: 410
<212> TYPE: DNA
<213> ORGANISM: Artificial Sequence
<220> FEATURE:
<223> OTHER INFORMATION: Artificial Polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
```

```
<222> LOCATION: (105)..(204)
<223> OTHER INFORMATION: any one or all of nucleic acids 105 - 204 can
      either be present or absent
<220> FEATURE:
<221> NAME/KEY: misc_feature
<222> LOCATION: (205)..(206)
<220> FEATURE:
<221> NAME/KEY: misc_feature
<222> LOCATION: (207)..(306)
<220> FEATURE:
<221> NAME/KEY: misc_feature
<222> LOCATION: (207)..(306)
<223> OTHER INFORMATION: n is a, c, g, or t
<220> FEATURE:
<221> NAME/KEY: misc_feature
<222> LOCATION: (307)..(406)
<223> OTHER INFORMATION: any one or all of nucleic acids 307 - 406 can
      either be present or absent
<220> FEATURE:
<221> NAME/KEY: misc_feature
<222> LOCATION: (407)..(410)

<400> SEQUENCE: 1

cctgnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnttnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnnnnnnn     360

nnnnnnnnnn nnnnnnnnnn nnnnnnnnnn nnnnnnnnnn nnnnnnttac                410


<210> SEQ ID NO 2
<211> LENGTH: 2010
<212> TYPE: DNA
<213> ORGANISM: Artificial Sequence
<220> FEATURE:
<223> OTHER INFORMATION: Artificial Polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(1004)
<223> OTHER INFORMATION: any one or all of nucleic acids 105 - 1004 can
      either be present or absent
<220> FEATURE:
<221> NAME/KEY: misc_feature
<222> LOCATION: (1005)..(1006)
<220> FEATURE:
<221> NAME/KEY: misc_feature
<222> LOCATION: (1007)..(1106)
<220> FEATURE:
<221> NAME/KEY: misc_feature
<222> LOCATION: (1007)..(1106)
<223> OTHER INFORMATION: n is a, c, g, or t
<220> FEATURE:
<221> NAME/KEY: misc_feature
<222> LOCATION: (1107)..(2006)
<223> OTHER INFORMATION: any one or all of nucleic acids 1107-2006 can
      either be present or absent
<220> FEATURE:
<221> NAME/KEY: misc_feature
<222> LOCATION: (2007)..(2010)
```

-continued

<400> SEQUENCE: 2

```
cctgnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnttnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnttac                                      2010
```

<210> SEQ ID NO 3
<211> LENGTH: 410
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(204)
<223> OTHER INFORMATION: any one or all of nucleic acids 105 - 204 can either be present or absent
<220> FEATURE:
<221> NAME/KEY: misc_feature
<222> LOCATION: (205)..(206)
<220> FEATURE:
<221> NAME/KEY: misc_feature
<222> LOCATION: (207)..(306)
<220> FEATURE:
<221> NAME/KEY: misc_feature
<222> LOCATION: (207)..(306)
<223> OTHER INFORMATION: n is a, c, g, or t
<220> FEATURE:
<221> NAME/KEY: misc_feature
<222> LOCATION: (307)..(406)
<223> OTHER INFORMATION: any one or all of nucleic acids 307-406 can either be present or absent
<220> FEATURE:
<221> NAME/KEY: misc_feature
<222> LOCATION: (407)..(410)

<400> SEQUENCE: 3
ggacnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnaannnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnaatg 410

<210> SEQ ID NO 4
<211> LENGTH: 2010
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(1004)
<223> OTHER INFORMATION: any one or all of nucleic acids 105-1004 can either be present or absent
<220> FEATURE:
<221> NAME/KEY: misc_feature
<222> LOCATION: (1005)..(1006)
<220> FEATURE:
<221> NAME/KEY: misc_feature
<222> LOCATION: (1007)..(1106)
<220> FEATURE:
<221> NAME/KEY: misc_feature
<222> LOCATION: (1007)..(1106)

-continued

<223> OTHER INFORMATION: n is a, c, g, or t
<220> FEATURE:
<221> NAME/KEY: misc_feature
<222> LOCATION: (1107)..(2006)
<223> OTHER INFORMATION: any one or all of nucleic acids 1107-2006 can
either be present or absent
<220> FEATURE:
<221> NAME/KEY: misc_feature
<222> LOCATION: (2007)..(2010)

<400> SEQUENCE: 4
ggacnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnaannnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnaatg 2010

<210> SEQ ID NO 5
<211> LENGTH: 410
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(204)
<223> OTHER INFORMATION: any one or all of nucleic acids 105 - 204 can
      either be present or absent
<220> FEATURE:
<221> NAME/KEY: misc_feature
<222> LOCATION: (205)..(206)
<220> FEATURE:
<221> NAME/KEY: misc_feature
<222> LOCATION: (207)..(306)
<220> FEATURE:
<221> NAME/KEY: misc_feature
<222> LOCATION: (207)..(306)
<223> OTHER INFORMATION: n is a, c, g, or t
<220> FEATURE:
<221> NAME/KEY: misc_feature
<222> LOCATION: (307)..(406)
<223> OTHER INFORMATION: any one or all of nucleic acids 307-406 can
      either be present or absent
<220> FEATURE:
<221> NAME/KEY: misc_feature
<222> LOCATION: (407)..(410)

<400> SEQUENCE: 5
cattnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnttnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnngtcc 410

<210> SEQ ID NO 6
<211> LENGTH: 410
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(204)
<223> OTHER INFORMATION: any one or all of nucleic acids 105 - 204 can either be present or absent
<220> FEATURE:
<221> NAME/KEY: misc_feature
<222> LOCATION: (205)..(206)
<220> FEATURE:
<221> NAME/KEY: misc_feature
<222> LOCATION: (207)..(306)
<220> FEATURE:
<221> NAME/KEY: misc_feature
<222> LOCATION: (207)..(306)
<223> OTHER INFORMATION: n is a, c, g, or t
<220> FEATURE:
<221> NAME/KEY: misc_feature
<222> LOCATION: (307)..(406)
<223> OTHER INFORMATION: any one or all of nucleic acids 307 - 406 can either be present or absent
<220> FEATURE:
<221> NAME/KEY: misc_feature
<222> LOCATION: (407)..(410)

<400> SEQUENCE: 6
gtaannnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnaannnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnncagg 410

<210> SEQ ID NO 7
<211> LENGTH: 2010
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(1004)
<223> OTHER INFORMATION: any one or all of nucleic acids 105-1004 can either be present or absent
<220> FEATURE:
<221> NAME/KEY: misc_feature
<222> LOCATION: (1005)..(1006)
<220> FEATURE:
<221> NAME/KEY: misc_feature
<222> LOCATION: (1007)..(1106)
<220> FEATURE:
<221> NAME/KEY: misc_feature
<222> LOCATION: (1007)..(1106)
<223> OTHER INFORMATION: n is a, c, g, or t
<220> FEATURE:
<221> NAME/KEY: misc_feature
<222> LOCATION: (1107)..(2006)
<223> OTHER INFORMATION: any one or all of nucleic acids 1107-2006 can either be present or absent
<220> FEATURE:
<221> NAME/KEY: misc_feature
<222> LOCATION: (2007)..(2010)

<400> SEQUENCE: 7

-continued

```
cattnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn nnnnnnnnnn nnnnnnnnnn nnnnnnnnnn nnnnnnnnnn    420

nnnnnnnnnn nnnnnnnnnn nnnnnnnnnn nnnnnnnnnn nnnnnnnnnn nnnnnnnnnn    480

nnnnnnnnnn nnnnnnnnnn nnnnnnnnnn nnnnnnnnnn nnnnnnnnnn nnnnnnnnnn    540

nnnnnnnnnn nnnnnnnnnn nnnnnnnnnn nnnnnnnnnn nnnnnnnnnn nnnnnnnnnn    600

nnnnnnnnnn nnnnnnnnnn nnnnnnnnnn nnnnnnnnnn nnnnnnnnnn nnnnnnnnnn    660

nnnnnnnnnn nnnnnnnnnn nnnnnnnnnn nnnnnnnnnn nnnnnnnnnn nnnnnnnnnn    720

nnnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnnn nnnnnnnnnn nnnnnnnnnn    960

nnnnnnnnnn nnnnnnnnnn nnnnnnnnnn nnnnnnnnnn nnnnttnnnn nnnnnnnnnn   1020

nnnnnnnnnn nnnnnnnnnn nnnnnnnnnn nnnnnnnnnn nnnnnnnnnn nnnnnnnnnn   1080

nnnnnnnnnn nnnnnnnnnn nnnnnnnnnn nnnnnnnnnn nnnnnnnnnn nnnnnnnnnn   1140

nnnnnnnnnn nnnnnnnnnn nnnnnnnnnn nnnnnnnnnn nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnnnnn nnnnnnnnnn   1380

nnnnnnnnnn nnnnnnnnnn nnnnnnnnnn nnnnnnnnnn nnnnnnnnnn nnnnnnnnnn   1440

nnnnnnnnnn nnnnnnnnnn nnnnnnnnnn nnnnnnnnnn nnnnnnnnnn nnnnnnnnnn   1500

nnnnnnnnnn nnnnnnnnnn nnnnnnnnnn nnnnnnnnnn nnnnnnnnnn nnnnnnnnnn   1560

nnnnnnnnnn nnnnnnnnnn nnnnnnnnnn nnnnnnnnnn nnnnnnnnnn nnnnnnnnnn   1620

nnnnnnnnnn nnnnnnnnnn nnnnnnnnnn nnnnnnnnnn nnnnnnnnnn nnnnnnnnnn   1680

nnnnnnnnnn nnnnnnnnnn nnnnnnnnnn nnnnnnnnnn nnnnnnnnnn nnnnnnnnnn   1740

nnnnnnnnnn nnnnnnnnnn nnnnnnnnnn nnnnnnnnnn nnnnnnnnnn nnnnnnnnnn   1800

nnnnnnnnnn nnnnnnnnnn nnnnnnnnnn nnnnnnnnnn nnnnnnnnnn nnnnnnnnnn   1860

nnnnnnnnnn nnnnnnnnnn nnnnnnnnnn nnnnnnnnnn nnnnnnnnnn nnnnnnnnnn   1920

nnnnnnnnnn nnnnnnnnnn nnnnnnnnnn nnnnnnnnnn nnnnnnnnnn nnnnnnnnnn   1980

nnnnnnnnnn nnnnnnnnnn nnnnnngtcc                                     2010
```

<210> SEQ ID NO 8
<211> LENGTH: 2010
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<220> FEATURE:

-continued

<221> NAME/KEY: misc_feature
<222> LOCATION: (5)..(104)
<220> FEATURE:
<221> NAME/KEY: misc_feature
<222> LOCATION: (5)..(104)
<223> OTHER INFORMATION: n is a, c, g, or t
<220> FEATURE:
<221> NAME/KEY: misc_feature
<222> LOCATION: (105)..(1004)
<223> OTHER INFORMATION: any one or all of nucleic acids 105-1004 can either be present or absent
<220> FEATURE:
<221> NAME/KEY: misc_feature
<222> LOCATION: (1005)..(1006)
<220> FEATURE:
<221> NAME/KEY: misc_feature
<222> LOCATION: (1007)..(1106)
<220> FEATURE:
<221> NAME/KEY: misc_feature
<222> LOCATION: (1007)..(1106)
<223> OTHER INFORMATION: n is a, c, g, or t
<220> FEATURE:
<221> NAME/KEY: misc_feature
<222> LOCATION: (1107)..(2006)
<223> OTHER INFORMATION: any one or all of nucleic acids 1107-2006 can either be present or absent
<220> FEATURE:
<221> NAME/KEY: misc_feature
<222> LOCATION: (2007)..(2010)

<400> SEQUENCE: 8
gtaannnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360
nnnnnnnnnn nnnnnnnnnn nnnnnnnnnn nnnnnnnnnn nnnnnnnnnn nnnnnnnnnn 420
nnnnnnnnnn nnnnnnnnnn nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnnn 540
nnnnnnnnnn nnnnnnnnnn nnnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnaannnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440

-continued

```
nnnnnnnnnn nnnnnnnnnn nnnnnnnnnn nnnnnnnnnn nnnnnnnnnn nnnnnnnnnn      1500

nnnnnnnnnn nnnnnnnnnn nnnnnnnnnn nnnnnnnnnn nnnnnnnnnn nnnnnnnnnn      1560

nnnnnnnnnn nnnnnnnnnn nnnnnnnnnn nnnnnnnnnn nnnnnnnnnn nnnnnnnnnn      1620

nnnnnnnnnn nnnnnnnnnn nnnnnnnnnn nnnnnnnnnn nnnnnnnnnn nnnnnnnnnn      1680

nnnnnnnnnn nnnnnnnnnn nnnnnnnnnn nnnnnnnnnn nnnnnnnnnn nnnnnnnnnn      1740

nnnnnnnnnn nnnnnnnnnn nnnnnnnnnn nnnnnnnnnn nnnnnnnnnn nnnnnnnnnn      1800

nnnnnnnnnn nnnnnnnnnn nnnnnnnnnn nnnnnnnnnn nnnnnnnnnn nnnnnnnnnn      1860

nnnnnnnnnn nnnnnnnnnn nnnnnnnnnn nnnnnnnnnn nnnnnnnnnn nnnnnnnnnn      1920

nnnnnnnnnn nnnnnnnnnn nnnnnnnnnn nnnnnnnnnn nnnnnnnnnn nnnnnnnnnn      1980

nnnnnnnnnn nnnnnnnnnn nnnnnncagg                                      2010
```

IN SITU NUCLEIC ACID AMPLIFICATION

CROSS-REFERENCE TO RELATED APPLICATIONS

This application is a continuation of PCT/US2021/031517, filed May 10, 2021, which claims the benefit of U.S. Provisional Application No. 63/023,752, filed May 12, 2020 which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Apr. 8, 2022, is named 051385-525C01US_ST25.txt and is 19,606 bytes in size.

BACKGROUND

Genetic analysis is taking on increasing importance in modern society as a diagnostic, prognostic, and as a forensic tool. Next generation sequencing (NGS) methods often rely on the amplification of genomic fragments hybridized to polynucleotide primers on a solid support. A majority of nucleic acid amplification techniques (e.g., DNA amplification) used in university, medical, and clinical laboratory research is performed using the polymerase chain reaction (PCR), though in the past decade alternative amplification methods have emerged that eliminate thermal cycling. Rolling circle amplification (RCA) is an efficient isothermal enzymatic process that generates long single stranded nucleic acid sequences. In RCA, a polymerase (e.g., Phi29, or Phi29 mutant) continuously extends a primer hybridized to a circular template by adding nucleotides at a relatively constant temperature (e.g., 37° C.). As the initial template molecule in RCA is circular, this displacement can continue, in theory infinitely, although there are practical limits to amplification.

Standard amplification methods employed in commercial sequencing devices (e.g., solid-phase bridge amplification), however, may suffer from a number of disadvantages. For example, standard bridge PCR has limited efficiency of re-priming (~30%) thereby limiting amplification efficiency. When performing temperature cycling on a solid-phase, the spatial proximity of amplicons to their reverse complement strands and the limited mobility of DNA primers favors the reannealing of full-length complementary strands as opposed to primer annealing. Furthermore, standard amplification protocols use a large amount of reagents, and generate relatively short reads per solid-phase DNA primer.

SUMMARY

In view of the foregoing, there is a need for improved methods of nucleic acid amplification. The present disclosure addresses this need, and provides additional benefits as well.

In an aspect, provided herein is a method of amplifying a polynucleotide for sequencing. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof on a solid support including a plurality of primers attached to the solid support, wherein the plurality of primers include a plurality of forward primers with complementarity to the first extension product and a plurality of reverse primers with complementarity to a complement of the first extension product, and the amplifying includes a plurality of cycles of strand denaturation, primer hybridization, and primer extension.

In an aspect, provided herein is a method of amplifying a polynucleotide for sequencing. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof on a solid support including a plurality of primers attached to the solid support, wherein the plurality of primers include a plurality of forward primers with complementarity to the first extension product and a plurality of reverse primers with complementarity to a complement of the first extension product, and further includes (i) extension of a 3' end of a first substrate-bound primer extension product hybridized to a second substrate-bound primer extension product, and/or (ii) extension of a 3' end of a third substrate-bound primer extension product hybridized to itself; and the amplifying includes a plurality of cycles of strand denaturation, primer hybridization, and primer extension.

In an aspect, provided herein is a method of amplifying a polynucleotide of a cell in situ for sequencing including: (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof in a cell, the cell including a plurality of immobilized primers, wherein the plurality of immobilized primers includes a plurality of forward primers with complementarity to the first extension product and a plurality of reverse primers with complementarity to a complement of the first extension product, and the amplifying includes a plurality of cycles of strand denaturation, primer hybridization, and primer extension.

In an aspect, provided herein is a method of amplifying a polynucleotide of a cell in situ for sequencing including: (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof in a cell, said cell including a plurality of immobilized primers, wherein the plurality of immobilized primers includes a plurality of forward primers with complementarity to the first extension product and a plurality of reverse primers with complementarity to a complement of the first extension product, and further includes (i) extension of a 3' end of a first immobilized primer extension product hybridized to a second immobilized primer extension product, and/or (ii) extension of a 3' end of a third immobilized primer extension product hybridized to itself; and the amplifying includes a plurality of cycles of strand denaturation, primer hybridization, and primer extension.

In an aspect, provided herein is a composition including a polynucleotide and a solid support. In embodiments, the composition includes (a) a first extension product including multiple complements of a template polynucleotide; and (b) a solid support including a plurality primers attached to the solid support, wherein the plurality of primers include a plurality of forward primers with complementarity to the first extension product and a plurality of reverse primers with complementarity to a complement of the first extension product.

In an aspect, provided herein is a composition including a polynucleotide and a solid support. In embodiments, the composition includes (a) a first in situ extension product including multiple complements of a template polynucleotide; and (b) a cell including a plurality of immobilized primers, wherein the plurality of immobilized primers include a plurality of forward primers with complementarity to the first in situ extension product and a plurality of reverse primers with complementarity to a complement of the first in situ extension product. In embodiments, the immobilized primers are attached to the cell. In embodiments, the immobilized primer is attached to an exogenous substrate within the cell.

In an aspect, provided herein are kits including one or more compositions disclosed herein.

BRIEF DESCRIPTION OF THE DRAWINGS

FIG. 7B. Clusters produced using 10 minutes eRCA, followed by 45 cycles of c-bPCR.

DETAILED DESCRIPTION

Figure 1A:
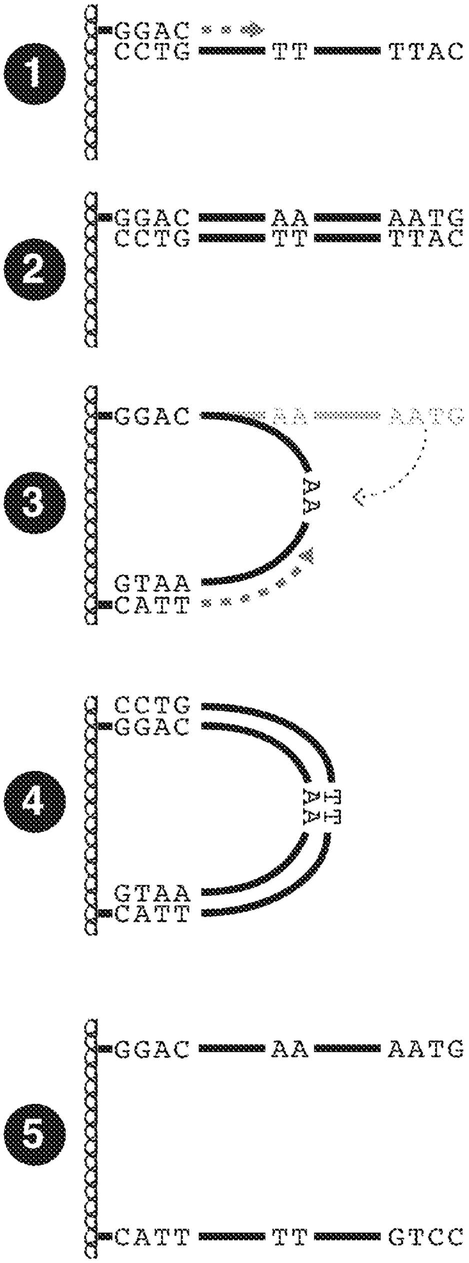
FIG. 1A. A diagram of cycle 1 of conventional bridge PCR (bPCR) amplification. A single-stranded linear template is hybridized to a surface-immobilized primer (1). After the initial extension (2) and removal of the linear template, the now covalently attached complementary strand is able to "bridge" over and hybridize to a second surface-immobilized primer (3). Extension off this priming site (4), followed by the addition of the denaturant results in two surface-immobilized complementary strands that are ready to participate in subsequent rounds of amplification (5). The template molecules depicted in this—and future—diagrams are over-simplified to only show the relevant structures for illustration purposes ("GGAC" represents "surface primer 1", "CATT" represents "surface primer 2", and "TT" represents a random fragment that has been ligated to universal adapters included in typical library prep). The lines connecting these sequences are not to scale and represent a plurality of nucleotides (e.g., approximately 100-200 nucleotides) that contain both the rest of the universal adapters as well as the rest the polynucleotide fragment inserted between them.

In embodiments, methods of DNA amplification described herein include at least two distinct amplification phases. In a first amplification phase, a primer extension product containing multiple copies of the initial nucleic acid template molecule (also referred to herein as an amplicon or concatemer) is made with the use of a primer (e.g., a surface-bound primer) and a DNA polymerase (e.g., strand-displacing DNA polymerase). Alternatively, the concatemer is formed with a solution-phase primer (e.g., RCA amplification is performed in solution and that resultant concatemer is then transferred to the solid-phase for the second amplification phase, such as thermal bPCR). Importantly, the resulting initial amplicon or amplicons contain multiple copies of the initial template molecule on the same nucleic acid strand. Subsequently, the initial amplicon or amplicons (i.e., the concatemer) participate in a second amplification phase in which multiple copies of the initial amplicon or amplicons are made via the hybridization of their respective free 3' end(s) to other solid-phase primers or to a complementary fraction of another amplicon, followed by extension by a DNA polymerase. During this second amplification phase, amplicons can be copied and result in nucleic acid molecules of the same length, or amplicons can hybridize to a complementary region of other DNA amplicons, thereby making the participating amplicons longer during the process. On a surface with multiple concatemers, both types of extension events may occur for different individual molecules during a given cycle, and over the course of many cycles, a given concatemer may participate in both types of extension events.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms “a”, “an”, and “the” include the plural reference unless the context clearly indicates otherwise.

Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term “about” means a range of values including the specified value, which a person of ordinary skill in the art would consider reasonably similar to the specified value. In embodiments, the term “about” means within a standard deviation using measurements generally acceptable in the art. In embodiments, about means a range extending to +/−10% of the specified value. In embodiments, about means the specified value.

Throughout this specification, unless the context requires otherwise, the words “comprise”, “comprises” and “comprising” will be understood to imply the inclusion of a stated step or element or group of steps or elements but not the exclusion of any other step or element or group of steps or elements. By “consisting of” is meant including, and limited to, whatever follows the phrase “consisting of.” Thus, the phrase “consisting of” indicates that the listed elements are required or mandatory, and that no other elements may be present. By “consisting essentially of” is meant including any elements listed after the phrase, and limited to other elements that do not interfere with or contribute to the activity or action specified in the disclosure for the listed elements. Thus, the phrase “consisting essentially of” indicates that the listed elements are required or mandatory, but that no other elements are optional and may or may not be present depending upon whether or not they affect the activity or action of the listed elements.

As used herein, the term “control” or “control experiment” is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term “associated” or “associated with” can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are “tethered”, “coated”, “attached”, or “immobilized” to one another or to a common solid or semisolid support. An association may refer to covalent or non-covalent means for attaching labels to solid or semi-solid supports such as beads. In embodiments, primers on or bound to a solid support are covalently attached to the solid support. An association may comprise hybridization between a target and a label.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme (e.g., a DNA polymerase).

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge PCR amplification, emulsion PCR, WildFire amplification (e.g., US patent publication US20130012399), and the like, or combinations thereof.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In some embodiments, a nucleic acid comprises a capture nucleic acid. A capture nucleic acid refers to a nucleic acid that is attached to a substrate. In some embodiments, a capture nucleic acid comprises a primer. In some embodiments, a capture nucleic acid is a nucleic acid configured to specifically hybridize to a portion of one or more nucleic acid templates (e.g., a template of a library). In some embodiments a capture nucleic acid configured to specifically hybridize to a portion of one or more nucleic acid templates is substantially complementary to a suitable portion of a nucleic acid template, or an amplicon thereof. In some embodiments a capture nucleic acid is configured to specifically hybridize to a portion of an adapter, or a complement thereof. In some embodiments a capture nucleic acid, or portion thereof, is substantially complementary to a portion of an adapter, or a complement thereof. In embodiments, a capture nucleic acid is a probe oligonucleotide. Typically, a probe oligonucleotide is complementary to a target polynucleotide or portion thereof, and further comprises a label (such as a binding moiety) or is attached to a surface, such that hybridization to the probe oligonucleotide permits the selective isolation of probe-bound polynucleotides from unbound polynucleotides in a population. A probe oligonucleotide may or may not also be used as a primer.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue.

The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, Oligonucleotides and Analogues: a Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation).

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently $—NH_2$, $—CN$, $—CH_3$, $C_2$-$C_6$ allyl (e.g., $—CH_2—CH=CH_2$), methoxyalkyl (e.g., $—CH_2—O—CH_3$), or $—CH_2N_3$. In embodiments, the blocking moiety is attached to the 3' oxygen of the nucleotide and is independently

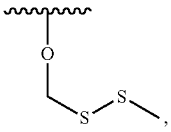,
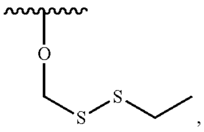,
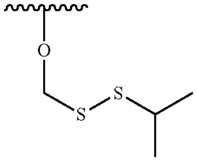,
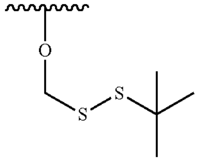,
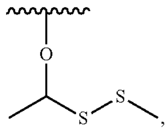,
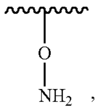,
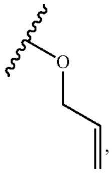,
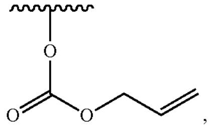,
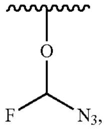,
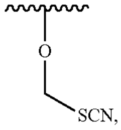, -continued

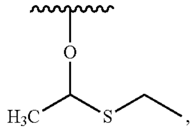,
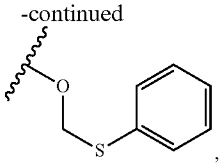,
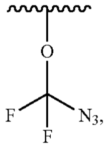,
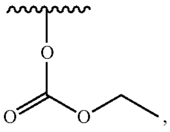,
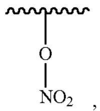,
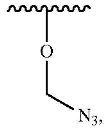 or
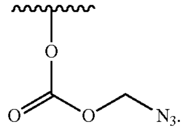.

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein 0 is the oxygen atom of the 3'-OH of the pentose and R is the blocking group, while the label is linked to the base, which acts as a reporter and can be cleaved. 3'-O-blocked reversible terminators are known in the art, and may be, for instance, a 3'-$ONH_2$ reversible terminator, a 3'-O-allyl reversible terminator, or a 3'-O-azidomethyl reversible terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.).

As used herein, the terms "solid support" and "substrate" and "solid surface" refers to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further comprise a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell.

The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flowcell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip), for example a metal surface (e.g. steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP. Magnets can be used to purify and/or capture nucleic acids bound to certain substrates (e.g., substrates comprising a metal or magnetic material).

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the compound's ability to cause a particular action, such as binding, to a particular molecular target with minimal or no action to other proteins in the cell.

In some embodiments, a nucleic acid (e.g., an adapter or a primer) includes a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads including the barcode can be identified as originating from a single sample polynucleotide molecule on the basis of the barcode alone. In other embodiments, individual barcode sequences may be used more than once, but adapters including the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined.

In embodiments, a nucleic acid (e.g., an adapter or primer) includes a sample barcode. In general, a "sample barcode" is a nucleotide sequence that is sufficiently different from other sample barcodes to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a nucleic acid, can be attached to a material, such as a hydrogel, polymer, or solid support, by a covalent or non-covalent bond. In embodiments, attachment is a covalent attachment.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS.* 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L4085/Y409A/P410V mutations, NEB Therminator IX DNA polymerase), or γ-phosphate labeled nucleotides (e.g., Therminator γ: D141A/E143A/W355A/L408W/R460A/Q4615/K464E/D480V/R484W/A485L). Typically, these enzymes do not have 5'-3' exonuclease activity. Additional information about thermophilic nucleic acid polymerases may be found in (Southworth M W, et al. *PNAS.* 1996; 93(11):5281-5285; Bergen K, et al. *ChemBioChem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3' →5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing reaction mixture" is used in accordance with its plain and ordinary meaning and refers to an aqueous mixture that contains the reagents necessary to add a nucleotide (e.g., s dNTP or dNTP analogue) to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The terms "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide that is capable of conferring biological function after being transcribed and/or translated.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium), toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide, -maleimide,

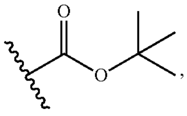, or 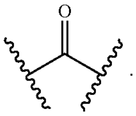.

In embodiments, the bioconjugate reactive group may be protected (e.g., with a protecting group). In embodiments, the bioconjugate reactive moiety is

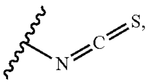 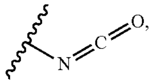 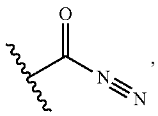,

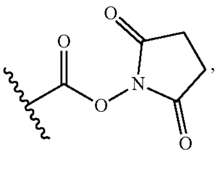, 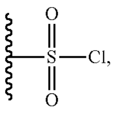 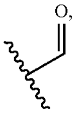

-continued

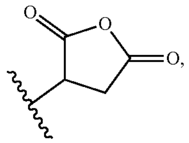, 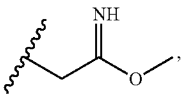, 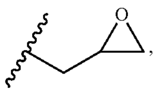,

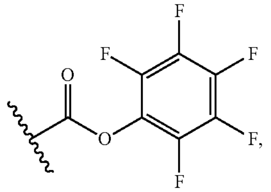

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term “bioconjugate” or “bioconjugate linker” refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 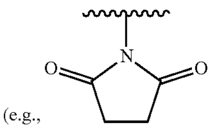), thereby forming a bioconjugate (e.g., 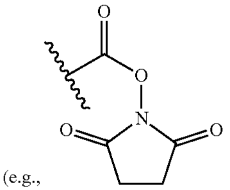).

In embodiments, the first bioconjugate reactive group (e.g., $-NH_2$) is covalently attached to the second bioconjugate reactive group (e.g., 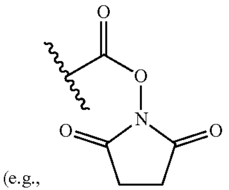 ), thereby forming a bioconjugate (e.g., 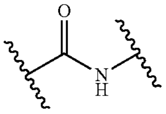 ).

In embodiments, the first bioconjugate reactive group (e.g., a coupling reagent) is covalently attached to the second bioconjugate reactive group (e.g., 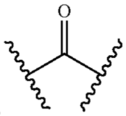 ), thereby forming a bioconjugate (e.g., 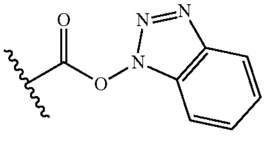 ).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate includes a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Methods

In an aspect, provided herein are methods of amplifying a template polynucleotide. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof on a solid support including a plurality of primers attached to the solid support, wherein the plurality of primers include a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, step (b) includes (i) extension of a 3' end of a first substrate-bound primer extension product hybridized to a second substrate-bound primer extension product, and/or (ii) extension of a 3' end of a third substrate-bound primer extension product hybridized to itself. In embodiments, step (b) includes (i) extension of a 3' end of a first substrate-bound primer extension product hybridized to a second substrate-bound primer extension product, and (ii) extension of a 3' end of a third substrate-bound primer extension product hybridized to itself. In embodiments, step (b) includes (i) extension of a 3' end of a first substrate-bound primer extension product hybridized to a second substrate-bound primer extension product, or (ii) extension of a 3' end of a third substrate-bound primer extension product hybridized to itself.

In an aspect, provided herein is a method of amplifying a polynucleotide for sequencing. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof on a solid support including a plurality of primers attached to the solid support, wherein the plurality of primers include a plurality of forward primers with complementarity to the first extension product and a plurality of reverse primers with complementarity to a complement of the first extension product, and further includes (i) extension of a 3' end of a first substrate-bound primer extension product hybridized to a second substrate-bound primer extension product, and/or (ii) extension of a 3' end of a third substrate-bound primer extension product hybridized to itself; and the amplifying includes a plurality of cycles of strand denaturation, primer hybridization, and primer extension.

In an aspect, provided herein are methods of amplifying a template polynucleotide of a cell in situ. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof in a cell, the cell including a plurality of immobilized primers, wherein the plurality of immobilized primers includes a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, step (b) includes (i) extension of a 3' end of a first immobilized primer extension product hybridized to a second immobilized primer extension product, and/or (ii) extension of a 3' end of a third immobilized primer extension product hybridized to itself.

In embodiments, the method includes forming the template polynucleotide. The template polynucleotide can be a circular, dumbbell-shaped, or other closed nucleic acid molecule configuration that does not have a free 3' or 5' end. Typical library preparation steps may be performed on a linear template such that it is circularized (e.g., such as the protocols described in Kershaw, C. J., & O'Keefe, R. T. (2012) 941, 257-269). The initial template polynucleotide molecules can vary length, such as about 100-300 nucleotides long, about 300-500 nucleotides long, or about 500-1000 nucleotides long. In embodiments, the initial template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the initial template polynucleotide molecule is about 150 nucleotides. In embodiments, the initial template polynucleotide is about 100-1000 nucleotides long. In embodiments, the initial template polynucleotide is about 25-75 nucleotides long. In embodiments, the initial template polynucleotide is about 75-100 nucleotides long. In embodiments, the initial template polynucleotide is about 100-300 nucleotides long. In embodiments, the initial template polynucleotide is about 300-500 nucleotides long. In embodiments, the initial template polynucleotide is about 500-1000 nucleotides long. In embodiments, the initial template polynucleotide molecule is about 25 nucleotides. In embodiments, the initial template polynucleotide molecule is about 75 nucleotides. In embodiments, the initial template polynucleotide molecule is about 100 nucleotides. In embodiments, the initial template polynucleotide molecule is about 300 nucleotides. In embodiments, the initial template polynucleotide molecule is about 500 nucleotides. In embodiments, the initial template polynucleotide molecule is about 1000 nucleotides.

In embodiments a source nucleic acid (e.g., genomic DNA) is treated to form single stranded linear fragments (e.g., about 50 to 600 nucleotides). Treatment typically entails fragmentation, such as by chemical fragmentation, enzymatic fragmentation, or mechanical fragmentation, followed by denaturation to produce single stranded DNA fragments. In embodiments, the template polynucleotide includes an adapter. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths.

In embodiments, the template polynucleotide includes single-stranded circular DNA. Methods for forming circular DNA templates are known in the art, for example linear polynucleotides are circularized in a non-template driven reaction with circularizing ligase, such as CircLigase, Taq DNA Ligase, HiFi Taq DNA Ligase, T4 ligase, or Ampligase® DNA Ligase. In embodiments, the method of forming the template polynucleotide includes ligating ends of a linear polynucleotide together. In embodiments, the two ends of the template polynucleotide are ligated directly together. In embodiments, the two ends of the template polynucleotide are ligated together with the aid of a bridging oligonucleotide (sometimes referred to as a splint oligonucleotide) that is complementary with the two ends of the template polynucleotide. In embodiments, the bridging oligonucleotide contains the amplification primer.

Circular polynucleotides of virtually any sequence can be produced using a variety of techniques (see for example U.S. Pat. No. 5,426,180; Dolinnaya et al. Nucleic Acids Research, 21: 5403-5407 (1993); or Rubin et al. Nucleic Acids Research, 23: 3547-3553 (1995), which are incorporated herein by reference). In embodiments, the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length. In embodiments, the circular polynucleotide is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides in length. In embodiments, the circular polynucleotide molecule is about 100-1000 nucleotides in length. In embodiments, the circular polynucleotide molecule is about 100-300 nucleotides in length. In embodiments, the circular polynucleotide molecule is about 300-500 nucleotides in length. In embodiments, the circular polynucleotide molecule is about 500-1000 nucleotides in length. In embodiments, the circular polynucleotide molecule is about 100 nucleotides. In embodiments, the initial template polynucleotide molecule is about 300 nucleotides. In embodiments, the circular polynucleotide molecule is about 500 nucleotides. In embodiments, the circular polynucleotide molecule is about 1000 nucleotides. Circular polynucleotides may be conveniently isolated by a conventional purification column, digestion of non-circular DNA by one or more appropriate exonucleases, or both.

In embodiments, the template polynucleotide includes double-stranded DNA. In embodiments, the method of forming the template polynucleotide includes ligating a hairpin adapter to an end of a linear polynucleotide. In embodiments, the method of forming the template polynucleotide includes ligating hairpin adapters to both ends of the linear polynucleotide. In embodiments, step a) occurs in solution. For example, a reaction mixture containing template polynucleotide, amplification primer, DNA polymerase (e.g., a strand-displacing polymerase), BSA, dNTPs, in DNA polymerase buffer, is incubated to generate a first extension product including multiple complements of the template polynucleotide. After generating the first extension product, they can be isolated and applied to a solid-support containing a plurality of primers for the formation of a random array. In embodiments, the first extension products are restricted to a specific region (referred to as a cluster) on the solid support which can be determined by controlling the placement of the plurality of primers attached thereto.

In some embodiments, the amplification primer is attached to the solid support. Amplification primer molecules can be fixed to surface by a variety of techniques, including covalent attachment and non-covalent attachment. In embodiments, the amplification primers are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term “interstitial region” refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have primers that exceeds the amount or concentration present at the interstitial regions. In some embodiments the primers may not be present at the interstitial regions. In embodiments, the amplification primer is attached to a solid support and a template polynucleotide is hybridized to the primer. In embodiments, at least two different primers are attached to the solid support (e.g., a forward and a reverse primer), which facilitates generating multiple amplification products from the first extension product or a complement thereof.

In embodiments of the methods provided herein, the clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 10-100 microns. In embodiments, the mean or median separation is about or at least about 10, 20, 30, 40, 50, 60, 70, 80, 90, 100 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is less than about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about 200-3000 nanometers. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 nanometers or a number or a range between any two of these values. In embodiments, the mean or median diameter is about 100-3000 nanometers. In embodiments, the mean or median diameter is about 100-2000 nanometers. In embodiments, the mean or median diameter is about 500-2500 nanometers. In embodiments, the mean or median diameter is about 200-1000 nanometers. In embodiments, the mean or median diameter is about 1000-2000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 1000 nanometers. In embodiments, the mean or median diameter is about or at most about 2000 nanometers. In embodiments, the mean or median diameter is about or at most about 2500 nanometers. In embodiments, the mean or median diameter is about or at most about 3000 nanometers.

In embodiments, the amplification primer includes one or more phosphorothioate nucleotides. In embodiments, the amplification primer includes a plurality of phosphorothioate nucleotides. In embodiments, about or at least about 20%, 30%, 40%, 50%, 60%, 70%, 80%, 90%, or about 100% of the nucleotides in the amplification primer are phosphorothioate nucleotides. In embodiments, most of the nucleotides in the amplification primer are phosphorothioate nucleotides. In embodiments, all of the nucleotides in the amplification primer are phosphorothioate nucleotides.

In embodiments, the primer includes a barcode that is 10-50, 20-30, or 4-12 nucleotides in length. In embodiments, the primer includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, step a) includes rolling circle amplification (RCA) (see, e.g., Lizardi et al., Nat. Genet. 19:225-232 (1998), which is incorporated herein by reference in its entirety). Several suitable RCA methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer).

In embodiments, step (a) includes exponential rolling circle amplification (eRCA). Exponential RCA is similar to the linear process except that it uses a second primer having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)).

In embodiments, step (a) includes hyperbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

In embodiments, the method includes amplifying a template polynucleotide by extending an amplification primer with a strand-displacing polymerase for about 10 seconds to about 30 minutes. In embodiments, the method includes amplifying a template polynucleotide by extending an amplification primer with a strand-displacing polymerase for about 30 seconds to about 16 minutes. In embodiments, the method includes amplifying a template polynucleotide by extending an amplification primer with a strand-displacing polymerase for about 30 seconds to about 10 minutes. In embodiments, the method includes amplifying a template polynucleotide by extending an amplification primer with a strand-displacing polymerase for about 30 seconds to about 5 minutes. In embodiments, the method includes amplifying a template polynucleotide by extending an amplification primer with a strand-displacing polymerase for about 1 second to about 5 minutes. In embodiments, the method includes amplifying a template polynucleotide by extending an amplification primer with a strand-displacing polymerase for about 1 second to about 2 minutes.

In embodiments, the method includes amplifying a template polynucleotide by extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C.

In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase phototolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase including at least one mutation selected from the group consisting of MBR, V51A, M97T, L123S, G197D, K209E, E221K, E239G, Q497P, K512E, E515A, and F526 (relative to wild type phi29 polymerase).

In embodiments, the strand-displacing polymerase is removed or inactivated (e.g., thermally inactivated or chemically inactivated) prior to step (b).

In embodiments, the method includes cleaving the first extension product prior to step (b). For example, in embodiments disclosed herein relating to cleaving the first extension product, step (a) includes incorporating one or more cleavable site into the template polynucleotide. The one or more cleavable sites may include a modified nucleotide, ribonucleotide, or a sequence containing a modified or unmodified nucleotide that is specifically recognized by a cleavage agent. The cleavable site(s) may be deoxyuracil triphosphate (dUTP), deoxy-8-Oxo-guanine triphosphate (d-8-oxoG), or other modified nucleotide(s), such as those described, for example, in US 2012/0238738, which is incorporated herein by reference for all purposes. In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent. In embodiments, the cleavable site includes one or more ribonucleotides. In embodiments, the cleavable site includes 2 to 5 ribonucleotides. In embodiments, the cleavable site includes one ribonucleotide. In embodiments, the cleavable sites can be cleaved at or near a modified nucleotide or bond by enzymes or chemical reagents, collectively referred to here and in the claims as "cleaving agents." Examples of cleaving agents include DNA repair enzymes, glycosylases, DNA cleaving endonucleases, or ribonucleases. For example, cleavage at dUTP may be achieved using uracil DNA glycosylase and endonuclease VIII (USER™, NEB, Ipswich, Mass.), as described in U.S. Pat. No. 7,435,572. In embodiments, when the modified nucleotide is a ribonucleotide, the cleavable site can be cleaved with an endoribonuclease. In embodiments, cleaving an extension product includes contacting the cleavable site with a cleaving agent, wherein the cleaving agent includes a reducing agent, sodium periodate, RNase, formamidopyrimidine DNA glycosylase (Fpg), endonuclease, restriction enzyme, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C.

In embodiments, step (b) includes amplification methodologies described herein or known in the art to amplify the products of the first amplification reaction. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments generated from the first amplification method of the two-step method described herein.

In embodiments, step (b) includes addition of a second polymerase. In embodiments, the second polymerase is different than the polymerase used in step (a). In embodiments, the polymerase is an archaeal DNA polymerases. In embodiments, the polymerase is Bst DNA Polymerase, Vent (exo-) DNA Polymerase, Pfu DNA polymerase, Taq polymerase, Phusion High-Fidelity DNA Polymerase, Q5 High-Fidelity DNA Polymerase, or mutant of any one of the foregoing. In embodiments, the polymerase is Bst DNA Polymerase, Vent (exo-) DNA Polymerase, Phusion High-Fidelity DNA Polymerase, or Q5 High-Fidelity DNA Polymerase.

Figure 1B:
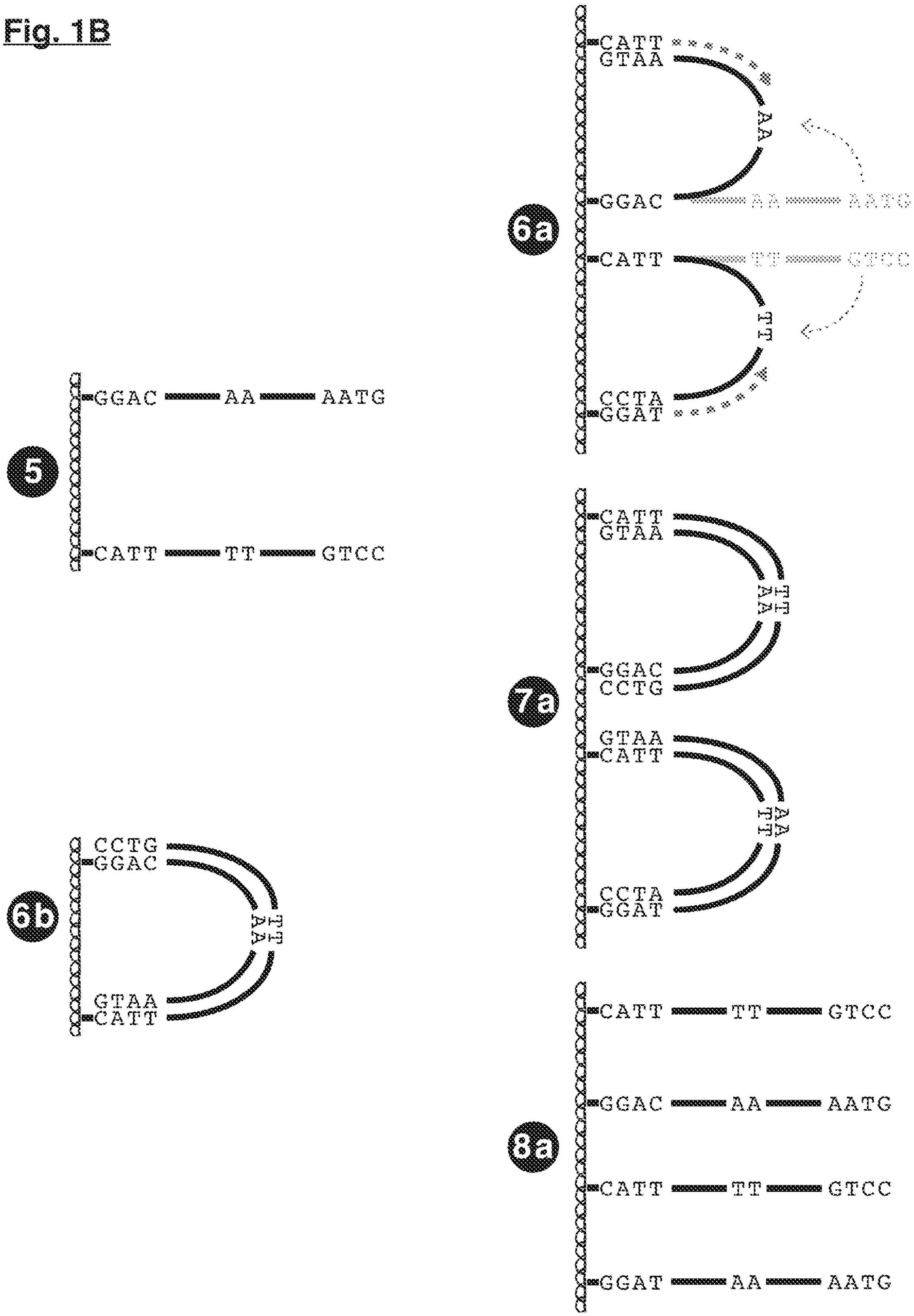
FIG. 1B. A diagram of cycle 2 of conventional bPCR. After denaturation of the initial complementary strands (5), two outcomes are possible. The 3' ends of the strands may hybridize to nearby surface primers (6a) where a second round of amplification can occur (7a). After the addition of the denaturant, a second set of complementary strands are ready to participate in subsequent rounds of amplification (8a). However, due to their proximity on the surface, the complementary strands may also undesirably rehybridize to each other (6b), in which no amplification will occur.
Figure 2A:
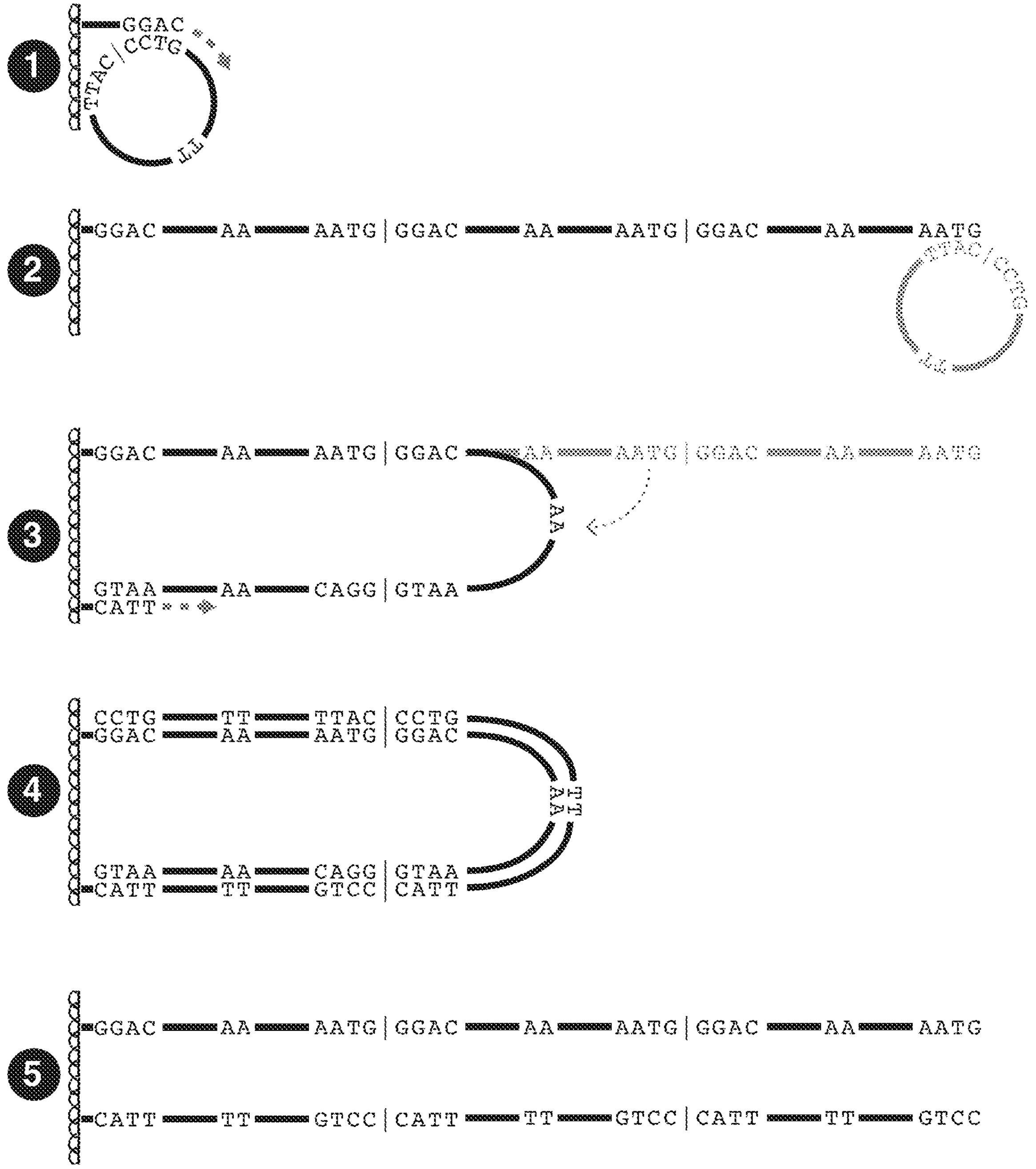
FIG. 2A. A diagram of an initial round of isothermal amplification followed by bPCR cycle 1 in hybrid amplification, in accordance with an embodiment of the present disclosure. A single-stranded circular template is hybridized to a surface-immobilized primer (1). Through the use of a strand-displacing DNA polymerase, the circular template is continuously amplified, forming a long single-stranded linear template consisting of multiple tandem copies of the complementary sequence (also referred to herein as "concatemers") (2). This concatemer is able to "bridge" over and hybridize to a second surface-immobilized primer (3). Extension off this priming site (4), followed by the addition of the denaturant results in two complementary strands that are ready to participate in subsequent rounds of amplification (5). A fundamental difference with respect to the products formed in conventional bPCR is that these strands are both concatemers.
Figure 2B:
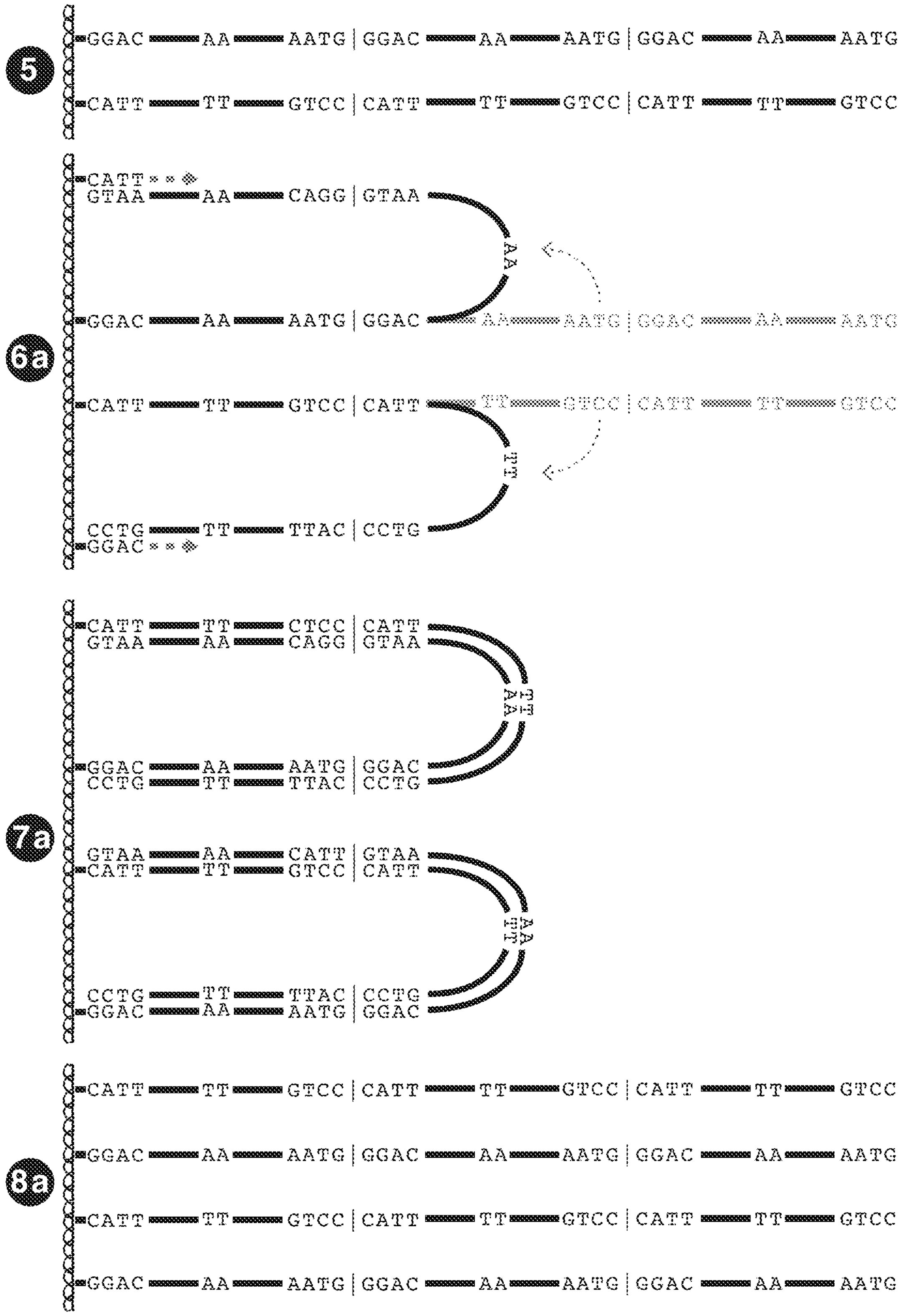
FIG. 2B. A diagram of one outcome that may occur in cycle 2 of hybrid amplification, according to an embodiment. After denaturation of the initial complementary strands (5), the 3' ends of the strands may hybridize to nearby surface primers (6a) where a second round of amplification can occur (7a). After the addition of the denaturant, a second set of complementary strands are ready to participate in subsequent rounds of amplification (8a).
Figure 2C:
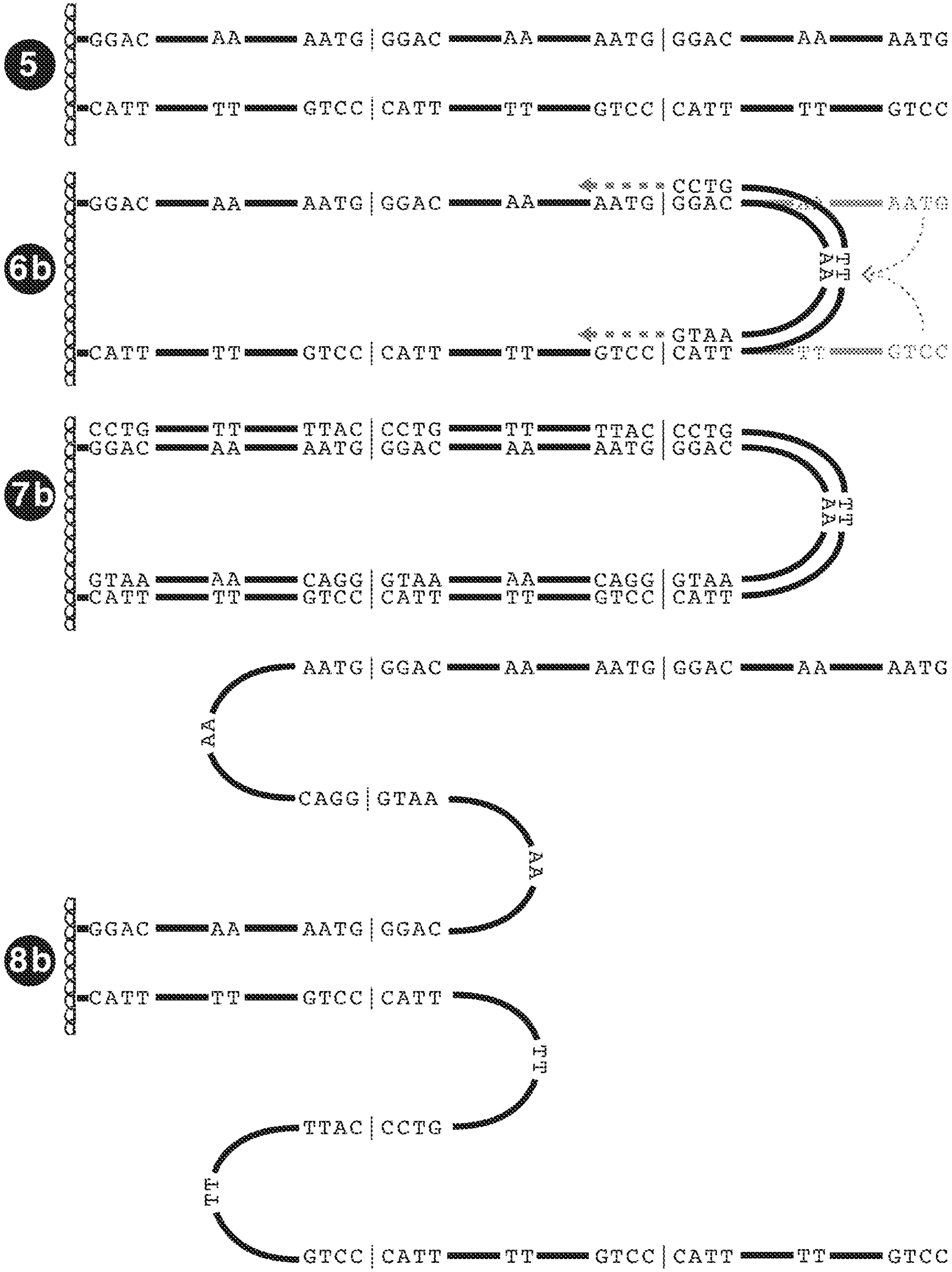
FIG. 2C. A diagram of an outcome that may occur in cycle 2 of hybrid amplification that is not possible in conventional bPCR. After denaturation (5), the strands may still rehybridize to each other; however, since these strands are concatemers of the initial amplicon, the 3' ends have the opportunity to hybridize at two or more locations along the complementary strand, not just at the end (6b). This incomplete hybridization results in 5' overhangs that are extendable during amplification (7b). While no new surface-bound strands will be formed, the initial starting strands will be elongated, thus still increasing the total amount of amplicons formed within the cluster (8b), and available for sequencing.

In embodiments, step (b) includes bridge amplification; for example as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers are attached to the solid support, the extension products released upon separation from an initial template are also attached to the solid support. Both strands are immobilized on the solid support at the 5' end, preferably via a covalent attachment (e.g., see FIGS. 1A-1B). The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing a polymerase in buffer conditions that allow primer annealing and extension. In embodiments, forward and/or reverse primers hybridize to primer binding sites that are specific to a particular target nucleic acid sequence present in the first extension product of step (a). In embodiments, forward and/or reverse primers hybridize to primer binding sites that are common among different first extension products of step (a). In embodiments, a portion of the forward primers (i.e., a fraction of the total number of forward primers) include a 3' modification to prevent extension in step (a). In embodiments, after step (a) the 3' modification is removed and the forward primers may extended in step (b). In embodiments, the 3' modification is a C3, C9, C12, or C18 spacer phosphoramidite, a 3'phosphate, a C3, C6, C12 amino modifier, or a reversible blocking moiety (e.g., reversible blocking moieties are described in U.S. Pat. Nos. 7,541,444 and 7,057,026). In embodiments, the 3' modification is a 3'-phosphate modification includes a 3' phosphate moiety, which is removed by a PNK enzyme.

In embodiments, step (b) includes thermal bridge polymerase chain reaction (t-bPCR) amplification. In embodiments, step (b) includes incubation in an additive that lowers a DNA denaturation temperature. In embodiments, the additive is betaine, dimethyl sulfoxide (DMSO), ethylene glycol, formamide, glycerol, guanidine thiocyanate, 4-methylmorpholine 4-oxide (NMO), or a mixture thereof. In embodiments, the additive is betaine, DMSO, ethylene glycol, or a mixture thereof. In embodiments, the additive is betaine, DMSO, or ethylene glycol.

In embodiments, step (b) includes chemical bridge polymerase chain reaction (c-bPCR) amplification. In embodiments, step (b) includes denaturation using a chemical denaturant. In embodiments, step (b) includes denaturation using acetic acid, hydrochloric acid, nitric acid, formamide, guanidine, sodium salicylate, sodium hydroxide, dimethyl sulfoxide (DMSO), propylene glycol, urea, or a mixture thereof. In embodiments, the chemical denaturant is sodium hydroxide or formamide. In embodiments, step (b) includes thermal bridge polymerase chain reaction (t-bPCR) amplification. In embodiments, step (b) includes chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a significantly lower concentration than traditional chemical bridge polymerase chain reactions.

In embodiments, step (b) includes fluidic cycling between an extension mixture that includes a polymerase and dNTPs, and a chemical denaturant. In embodiments, the polymerase is a strand-displacing polymerase or a non-strand displacing polymerase. In embodiments, the solutions are thermally cycled between about 40° C. to about 65° C. during fluidic cycling of the extension mixture and the chemical denaturant. For example, the extension cycle is maintained at a temperature of 55° C.-65° C., followed by a denaturation cycle that is maintained at a temperature of 40° C.-65° C., or by a denaturation step in which the temperature starts at 60° C.-65° C. and is ramped down to 40° C. prior to exchanging the reagent. In embodiments, step (b) includes modulating the reaction temperature prior to initiating the next cycle. In embodiments, the denaturation cycle and/or the extension cycle is maintained at a temperature for a sufficient amount of time, and prior to starting the next cycle the temperature is modulated (e.g., increased relative to the starting temperature or reduced relative to the starting temperature). In embodiments, the denaturation cycle is performed at a temperature of 60° C.-65° C. for about 5-45 sec, then the temperature is reduced (e.g., lowered to about 40° C.) before starting an extension cycle (i.e., before introducing an extension mixture). Lowering the temperature, even in the presence of a chemical denaturant, facilitates primer hybridization in the subsequent step when the amplicons are exposed to conditions that promote hybridization. In embodiments, the extension cycle is performed at a temperature of 50° C.-60° C. for about 0.5-2 minutes, then the temperature is increased (e.g., raised to between about 60° C. to about 70° C., or to about 65° C. to about 72° C.) after introducing the extension mixture. In embodiments, the cycling between the extension mixture and the chemical denaturant is performed at least 5, at least 10, at least 20, at least 30, at least 40, at least 50, at least 75, at least 100, or at least 200 times. In embodiments, the cycling between the extension mixture and the chemical denaturant is performed about 5, about 10, about 20, about 30, about 40, about 50, about 75, about 100, or about 200 times. In embodiments, the cycling between the extension mixture and the chemical denaturant is performed a total of 5, 10, 20, 30, 40, 50, 75, 100, 200, or more times. In embodiments, the fluidic cycling is performed in the presence of about 2 to about 15 mM Mg'. In embodiments, the fluidic cycling is performed in the presence of about 2, about 3, about 4, about 5, about 6, about 7, about 8, about 9, about 10, about 11, about 12, about 13, about 14, or about 15 mM $Mg^{2+}$.

In embodiments, step (b) describes amplifying the first extension product or a complement thereof on a solid support, wherein amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the concatemer. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles.

In embodiments, step (b) describes a plurality of strand denaturation cycles, wherein the initial denaturation cycle is at different conditions from the remaining denaturation cycles. For example, in embodiments, the initial denaturation cycle is at about 85° C.-95° C. for about 1 minute to about 10 minutes, whereas denaturation in the remaining cycles is different (e.g. about 85° C. for about 15-30 sec). In embodiments, step (b) includes an initial denaturation at about 85° C.-95° C. for about 5 minutes to about 10 minutes. In embodiments, step (b) includes an initial denaturation at 90° C.-95° C. for about 1 to 10 minutes. In embodiments, step (b) includes an initial denaturation at 80° C.-85° C. for about 1 to 10 minutes. In embodiments, step (b) includes an initial denaturation at 85° C.-90° C. for about 1 to 10 minutes.

In embodiments, the plurality of cycles includes thermally cycling between (i) about 80° C. to 90° C. for denaturation, and (ii) about 55° C. to about 65° C. for annealing/extension of the primer. In embodiments, the plurality of cycles includes thermally cycling between (i) about 85° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer. In embodiments, the plurality of cycles includes thermally cycling between (i) less than 80° C. (e.g., 70 to 80° C.) for denaturation, and (ii) about 55° C. to about 65° C. for annealing/extension of the primer. In embodiments, the plurality of cycles includes thermally cycling between (i) about 70° C. for denaturation, and (ii) about 65° C. for annealing/extension of the primer. In embodiments, the plurality of cycles includes thermally cycling between (i) about 75° C. for denaturation, and (ii) about 55° C. for annealing/extension of the primer. In embodiments, the plurality of cycles includes thermally cycling between (i)

about 85° C. for denaturation, and (ii) about 65° C. for annealing/extension of the primer.

In embodiments, the plurality of cycles includes thermally cycling between (i) about 85° C. for less than 1 minute for denaturation, and (ii) about 65° C. for about 1 to 2 minutes for annealing/extension of the primer. In embodiments, the plurality of cycles includes thermally cycling between (i) about 85° C. for less than 1 minute for denaturation, and (ii) about 60° C. to about 65° C. for about 1 minute for annealing/extension of the primer. In embodiments, the plurality of cycles includes thermally cycling between (i) about 85° C. for about 15-30 sec for denaturation and (ii) about 65° C. for about 1 minute for annealing/extension of the primer. In embodiments, the plurality of cycles includes thermally cycling between (i) about 85° C. for about 30 sec for denaturation and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer. In embodiments, the plurality of cycles includes thermally cycling between (i) about 85° C. for about 15-30 sec for denaturation, and (ii) about 65° C. for about 1 minute for annealing/extension of the primer.

In embodiments, the plurality of denaturation steps is at a temperature of about 80° C.-95° C. In embodiments, the plurality of denaturation steps is at a temperature of about 80° C.-90° C. In embodiments, the plurality of denaturation steps is at a temperature of about 85° C.-90° C. In embodiments, the plurality of denaturation steps is at a temperature of about 81° C., 82° C., 83° C., 84° C., 85° C., 86° C., 87° C., 88° C., 89° C., or about 90° C. In embodiments, the plurality of denaturation steps is at a temperature of about 70° C.-85° C. In embodiments, the plurality of denaturation steps is at a temperature of about 70° C.-80° C. In embodiments, the plurality of denaturation steps is at a temperature of about 75° C.-80° C. In embodiments, the plurality of denaturation steps is at a temperature of about 70° C., 71° C., 72° C., 73° C., 74° C., 75° C., 76° C., 77° C., 78° C., 79° C., or about 80° C. In embodiments, the annealing/extension of the primer cycle is at a temperature of about 55° C., 56° C., 57° C., 58° C., 59° C., 60° C., 61° C., 62° C., 63° C., 64° C., or about 65° C.

In embodiments, the method further includes sequencing the amplification products of step (b). A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

A number of new techniques have been described for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization), FISSEQ (fluorescent in situ sequencing), and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; Lee J H et al. Nat. Protoc. 2015; 10(3):442-58); and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

In an aspect, provided herein are methods of sequencing a template polynucleotide. In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof on a solid support including a plurality of primers attached to the solid support, wherein the plurality of primers include a plurality of forward primers with complementarity to the first extension product and a plurality of reverse primers with complementarity to a complement of the first extension product, and the amplifying includes a plurality of cycles of strand denaturation, primer hybridization, and primer extension to generate amplification products (alternatively referred to as clusters); and (c) sequencing the amplification products.

In embodiments, the method includes (a) amplifying a template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; (b) amplifying the first extension product or a complement thereof in a cell in situ wherein the cell includes a plurality of immobilized primers, wherein the plurality of immobilized primers include a plurality of forward primers with complementarity to the first extension product and a plurality of reverse primers with complementarity to a complement of the first extension product, and the amplifying includes a plurality of cycles of strand denaturation, primer hybridization, and primer extension to generate amplification products (alternatively referred to as clusters); and (c) sequencing the amplification products.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, the primer is covalently attached to the solid support. In embodiments, the 5' end of the primer contains a functional group that is tethered to the solid support. Non-limiting examples of covalent attachment include amine-modified polynucleotides reacting with epoxy or isothiocyanate groups on the solid support, succinylated polynucleotides reacting with aminophenyl or aminopropyl functional groups on the solid support, dibenzocycloctyne-modified polynucleotides reacting with azide functional groups on the solid support (or vice versa), trans-cyclooctyne-modified polynucleotides reacting with tetrazine or methyl tetrazine groups on the solid support (or vice versa), disulfide modified polynucleotides reacting with mercapto-functional groups on the solid support, amine-functionalized polynucleotides reacting with carboxylic acid groups on the solid support via 1-ethyl-3-(3-dimethylaminopropyl)-carbodiimide hydrochloride (EDC) chemistry, thiol-modified polynucleotides attaching to a solid support via a disulphide bond or maleimide linkage, alkyne-modified polynucleotides attaching to a solid support via copper-catalyzed click reactions to azide functional groups on the solid support, and acrydite-modified polynucleotides polymerizing with free acrylic acid monomers on the solid support to form polyacrylamide or reacting with thiol groups on the solid support. In embodiments, the primer is attached to the solid support polymer through electrostatic binding. For example, the negatively charged phosphate backbone of the primer may be bound electrostatically to positively charged monomers in the solid support.

In embodiments, the primer includes a first bioconjugate reactive group. In embodiments, the primer is attached to a cellular compartment. In embodiments, the cellular component includes a second bioconjugate reactive group. In embodiments, the first bioconjugate reactive group is attached to the second bioconjugate reactive group by covalent or non-covalent bonding. In embodiments, the primer is covalently attached to a cellular component. In embodiments, the 5' end of the primer contains a functional group that is tethered to the cellular component. In embodiments, the primer is covalently attached to a matrix within the cell. In embodiments, the 5' end of the primer contains a functional group that is tethered to the matrix within the cell. Non-limiting examples of covalent attachment include amine-modified polynucleotides reacting with epoxy or isothiocyanate groups in the cell or matrix within the cell, succinylated polynucleotides reacting with aminophenyl or aminopropyl functional groups in the cell or matrix within the cell, dibenzocycloctyne-modified polynucleotides reacting with azide functional groups in the cell or matrix within the cell (or vice versa), trans-cyclooctyne-modified polynucleotides reacting with tetrazine or methyl tetrazine groups in the cell or matrix within the cell (or vice versa), disulfide modified polynucleotides reacting with mercapto-functional groups in the cell or matrix within the cell, amine-functionalized polynucleotides reacting with carboxylic acid groups in the cell or matrix within the cell via 1-ethyl-3-(3-dimethylaminopropyl)-carbodiimide hydrochloride (EDC) chemistry, thiol-modified polynucleotides attaching to cell or matrix within the cell via a disulphide bond or maleimide linkage, alkyne-modified polynucleotides attaching to the cell or matrix within the cell via copper-catalyzed click reactions to azide functional groups in the cell or matrix within the cell, and acrydite-modified polynucleotides polymerizing with free acrylic acid monomers in the cell or matrix within the cell to form polyacrylamide or reacting with thiol groups in the cell or matrix within the cell. In embodiments, the primer is attached to the polymer through electrostatic binding. For example, the negatively charged phosphate backbone of the primer may be bound electrostatically to positively charged monomers in the solid support.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US 2018/0274024, WO 2017/205336, US 2018/0258472, each of which are incorporated herein in their entirety for all purposes.

In embodiments, the methods of the invention herein are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 1-10 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell, a fungal cell, a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the cell is a stem cell, an immune cell, a cancer cell, a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell.

In embodiments, the cell is a prokaryotic cell. In embodiments, the cell is a bacterial cell. In embodiments, the bacterial cell is a *Bacteroides, Clostridium, Faecalibacterium, Eubacterium, Ruminococcus, Peptococcus, Peptostreptococcus*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the cell is a neuronal cell, an endothelial cell, epithelial cell, germ cell, plasma cell, a muscle cell, peripheral blood mononuclear cell (PBMC), a myocardial cell, or a retina cell.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the cell is a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNAT1, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the cell is a cell (e.g., a T cell) within a tumor. In embodiments, the cell is a non-allogenic cell (i.e., native cell to the subject) within a tumor. In embodiments, the cell is a tumor infiltrating lymphocyte (TIL). In embodiments, the cell is an allogenic cell. In embodiments, the cell is a circulating tumor cell.

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate.

In embodiments, the cell is immobilized to a substrate. Substrates can be two- or three-dimensional and can include a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a "matrix", "synthetic matrix", "exogenous polymer" or "exogenous hydrogel". In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate.

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissues include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol, HOPE®, CytoSkelFix™, F-Solv, FineFIX®, RCL2/KINFix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments the cell is lysed to release nucleic acid or other materials from the cells. For example, the cells may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the cell.

In embodiments, the method further includes subjecting the cell to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods.

In embodiments, the method further includes an amplification method for amplifying the circular polynucleotide. In embodiments, the method further includes amplifying the circular polynucleotide by extending an amplification primer with a polymerase (e.g., a strand-displacing polymerase), wherein the primer extension generates an extension product including multiple complements of the circular polynucleotide, referred to as an amplicon. An amplicon typically contains multiple, tandem copies of the circularized nucleic acid molecule of the corresponding sample nucleic acid. The number of copies can be varied by appropriate modification of the reaction conditions, such as varying the number of amplification cycles, using polymerases of varying processivity in the amplification reaction, or varying the length of time that the amplification reaction is run. In embodiments, the circular polynucleotide is copied about 5-50 times (i.e., the extension product includes about 5-50 complements of the circular polynucleotide). In embodiments, the circular polynucleotide is copied about 100-300 times (i.e., the extension product includes about 100 to 300 complements of the circular polynucleotide).

In embodiments, the method includes subjecting the cell to a polymer including a plurality of immobilized oligonucleotide primers (e.g., primers covalently attached to components within the matrix forming polymer). In embodiments, the method includes contacting the cell with a plurality of oligonucleotide primers that are capable of forming a covalent attachment to one or more cellular components; when the oligonucleotide primers form a covalent attachment to a cellular component, they may be referred to as immobilized oligonucleotide primers. In embodiments, the covalent attachment of the oligonucleotide primers to one or more cellular components does not require cross-linking. In embodiments, the attachment of the oligonucleotide primers to one or more cellular components includes hybridization of modified oligonucleotides (e.g., LNA-containing oligonucleotides that provide increased thermal hybridization stability). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocycloctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the matrix.

In embodiments, the plurality of oligonucleotide primers form covalent attachments to one or more cellular components through bioconjugate reactive moieties. In embodiments, the 5' end of the primer contains a functional group that is capable of reacting with a complementary group so the primer may be tethered to a cellular component (e.g., a protein). In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the matrix. In embodiments, the 3' end of the primer is covalently attached to a cellular component. In embodiments, the 3' end of the primer is covalently attached to the matrix. The primers can include one or more reactive moieties. As used herein, the term reactive moiety includes any group capable of reacting with another molecule, e.g., a nucleic acid or polypeptide through covalent, non-covalent or other interactions. By way of example, the primer can include an amino acid reactive moiety that reacts with an amino acid on a protein or polypeptide through a covalent, non-covalent or other interaction.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, and Pol I DNA polymerases. SD polymerase, Bst large fragment polymerase, or a phi29 polymerase or mutant thereof. In embodiments, the polymerase is a strand-displacing polymerase. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the 129 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. In embodiments, the polymerase is a phage or bacterial RNA polymerases (RNAPs). In embodiments, the polymerase is a T7 RNA polymerase. In embodiments, the polymerase is an RNA polymerase. Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the matrix in which the cell is embedded (e.g. a hydrogel). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NETS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., aminoallyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)9)).

In embodiments, the amplification primer and the sequencing primer includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers (e.g., amplification primer or sequencing primer) include nucleotides ranging from 17 to 30 nucleotides. In embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

In embodiments, one or more nucleotides within the amplification primer sequence, the sequencing primer sequence, and/or the immobilized oligonucleotide primer contains one or more functional moieties (e.g., bioconjugate reactive groups) that serve as attachment points to the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide (s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NETS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the amplification primer and/or the sequencing primer contains a modified nucleotide (e.g., aminoallyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive cross-linking agent with PEG spacers, such as (PEGylated bis (sulfosuccinimidyl)suberate) (BS(PEG)9)).

In embodiments, the method includes amplifying the circular polynucleotide by extending an amplification primer with a strand-displacing polymerase, wherein the primer extension generates an extension product including multiple complements of the circular polynucleotide. In embodiments, the method of amplifying includes an isothermal amplification method. In embodiments, the method of amplifying includes rolling circle amplification (RCA) or rolling circle transcription (RCT). In embodiments, the method of amplifying is rolling circle amplification (RCA). In embodiments, amplifying includes exponential rolling circle amplification (eRCA). Exponential RCA is similar to the linear process except that it uses a second primer (e.g., one or more immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)).

In embodiments, amplifying the circular oligonucleotide includes incubation with a strand-displacing polymerase. In embodiments, amplifying includes incubation with a strand-displacing polymerase for about 10 seconds to about 30 minutes. In embodiments, amplifying includes incubation with a strand-displacing polymerase at a temperature of about 20° C. to about 50° C. In embodiments, incubation with the strand-displacing polymerase is at a temperature of about 35° C. to 42° C. In embodiments, the strand-displacing polymerase is phi29 polymerase, SD polymerase, Bst large fragment polymerase, phi29 mutant polymerase, or a thermostable phi29 mutant polymerase.

In embodiments, the extension product includes three or more copies of the target nucleic acid. In embodiments, the extension product includes at least three or more copies of the target nucleic acid. In embodiments, the extension product includes at least five or more copies of the target nucleic acid. In embodiments, the extension product includes at 5 to 10 copies of the target nucleic acid. In embodiments, the extension product includes 10 to 20 copies of the target nucleic acid. In embodiments, the extension product includes 20 to 50 copies of the target nucleic acid.

Composition & Kits

In an aspect, provided herein is a composition including a polynucleotide and a solid support. In embodiments, the composition includes one or more elements described herein with regard to any of the various methods described herein. In embodiments, the composition includes (a) a first extension product including multiple complements of a template polynucleotide; and (b) a solid support including a plurality primers attached to the solid support, wherein the plurality of primers include a plurality of forward primers with complementarity to the first extension product and a plurality of reverse primers with complementarity to a complement of the first extension product. The first extension product, template, solid support, forward primers, and reverse primers can be any of those described herein, such as with regard to the various methods described herein.

In an aspect, provided herein is a composition including a polynucleotide and a solid support. In embodiments, the composition includes (a) a first in situ extension product including multiple complements of a template polynucleotide; and (b) a cell including a plurality of immobilized primers, wherein the plurality of immobilized primers include a plurality of forward primers with complementarity to the first in situ extension product and a plurality of reverse primers with complementarity to a complement of the first in situ extension product. The first in situ extension product, template, cell, forward primers, and reverse primers can be any of those described herein, such as with regard to the various methods described herein. In embodiments, the immobilized primers are attached to a cellular component or a matrix (e.g., a synthetic matrix) within the cell.

In embodiments, the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length.

In embodiments, the template polynucleotide includes one or more adapters. In embodiments, the adapter includes a hairpin loop structure.

In embodiments, the composition further includes a polymerase. In embodiments, the composition further includes a strand-displacing polymerase. In embodiments, the composition includes a strand-displacing polymerase, such as a phi29 polymerase, phi29 mutant polymerase or a thermostable phi29 mutant polymerase.

In embodiments, the composition further includes an additive that lowers a DNA denaturation temperature. In embodiments, the composition includes an additive such as betaine, dimethyl sulfoxide (DMSO), ethylene glycol, formamide, glycerol, guanidine thiocyanate, 4-methylmorpholine 4-oxide (NMO), or a mixture thereof.

In embodiments, the composition further includes a denaturant. The denaturant may be acetic acid, hydrochloric acid, nitric acid, formamide, guanidine, sodium salicylate, sodium hydroxide, dimethyl sulfoxide (DMSO), propylene glycol, urea, or a mixture thereof.

In embodiments, the solid support is glass or quartz, such as a microscope slide, having a surface that is uniformly silanized. This may be accomplished using conventional protocols e.g., Beattie et a (1995), Molecular Biotechnology, 4: 213. Such a surface is readily treated to permit end-attachment of primers (e.g., forward and reverse primers, and/or an amplification primer) prior to amplification. In embodiments the solid support surface further includes a polymer coating, which contains functional groups capable of immobilizing primers.

In some embodiments, the solid support includes a patterned surface suitable for immobilization of primers in an ordered pattern. A patterned surface refers to an arrangement of different regions in or on an exposed layer of a solid support. For example, one or more of the regions can be features where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the primers are randomly distributed upon the solid support. In some embodiments, the primers are distributed on a patterned surface.

In an aspect is provided a kit containing a composition as described herein, including embodiments. Generally, the kit includes one or more containers providing composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase enzyme, Taq DNA Ligase, HiFi Taq DNA Ligase, T4 ligase, or Ampligase DNA Ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 ligase, or Ampligase DNA Ligase), and (b) ligation enzyme cofactors. In embodiments, the kit further includes instructions.

In embodiments, the kit includes a plurality of primers (e.g., amplification primers, forward primers, reverse primers, and sequencing primers). Suitable primers of appropriate nucleotide sequence for use with the adapters included in the kit can be readily prepared using standard automated nucleic acid synthesis equipment and reagents in routine use in the art. The kit may include as supply of one single type of primer or separate supplies (e.g., a mixture) of two different primers, for example a pair of primers suitable amplification as described herein. Adapters and/or primers may be supplied in the kits ready for use, or more preferably as concentrates-requiring dilution before use, or even in a lyophilized or dried form requiring reconstitution prior to use. If required, the kits may further include a supply of a suitable diluent for dilution or reconstitution of the primers. Optionally, the kits may further include supplies of reagents, buffers, enzymes, and dNTPs for use in carrying out nucleic acid amplification. Further components which may optionally be supplied in the kit include sequencing primers suitable for sequencing templates prepared using the methods described herein.

EXAMPLES

As described herein is a solid-phase combination amplification (also referred to herein as a hybrid amplification, or two-step amplification) method to amplify nucleic acids to produce amplicons. The amplicons can be detected, for example, via a nucleic acid sequencing technique as set forth herein. The nucleic acids can be amplified using plurality of primers that are attached to a surface.

Described herein is the application of solid-phase PCR conditions to amplicons that contain multiple copies of the initial template strand on the same nucleic acid molecule (i.e., those amplicons formed via the first amplification method, a concatemer). This enables greater molecular flexibility and reach because of the longer initial amplicons, and allows hybridization of free 3' ends not only to other solid-phase DNA primers, but also to a complementary region of other DNA amplicons that may serve as template for further extension. This enhances the amount of re-priming/hybridization events, which greatly enhances the amplification efficiency compared to amplification with amplicons that contain only one copy of the initial nucleic acid molecule. At the end of the second amplification step, the resulting cluster of DNA amplicons contains multiple copies of the initial template molecule per amplicon strand. This is beneficial for DNA sequencing applications that rely on sequencing-by-synthesis (SBS), because it increases the density and allows more sequencing primers to be extended by a sequencing polymerase per cluster. Because more sequencing primers can be hybridized and extended within the same monoclonal cluster, greater fluorescence signals are produced per individual monoclonal cluster, which can result in higher signal-to-background ratios and improved sequencing results from said clusters.

Example 1. Hybrid Amplification Method

Typically, a single method of nucleic acid amplification, e.g., PCR only or eRCA only, is performed to generate amplicons. We found, however, that performing a combination of amplification techniques, for example at least one cycle of rolling circle amplification followed by at least one cycle of PCR amplification (e.g., bridge PCR with thermal or chemical denaturing), or one cycle of an isothermal amplification method results in denser, and in the context of nucleic acid sequencing, brighter monoclonal clusters. This combination of two amplification methods (referred to herein as hybrid amplification) is significantly better than performing one amplification method to generate clusters.

Figure 3A:
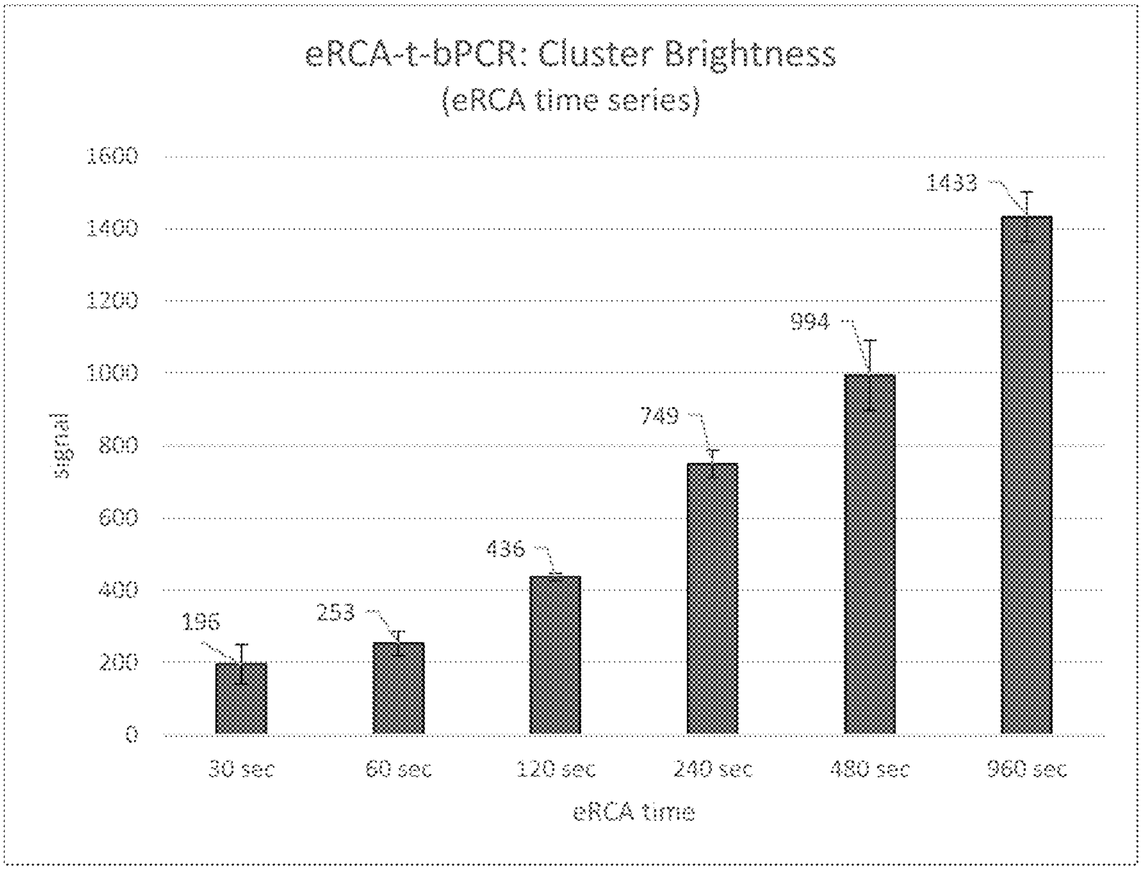
FIG. 3A. A graph highlighting the positive correlation between cluster brightness and exponential RCA (eRCA) time. While all timepoints formed clusters, clusters produced with the 960 sec eRCA starting product were 10× brighter than those formed with the 30 sec eRCA starting product.
Figure 3B:
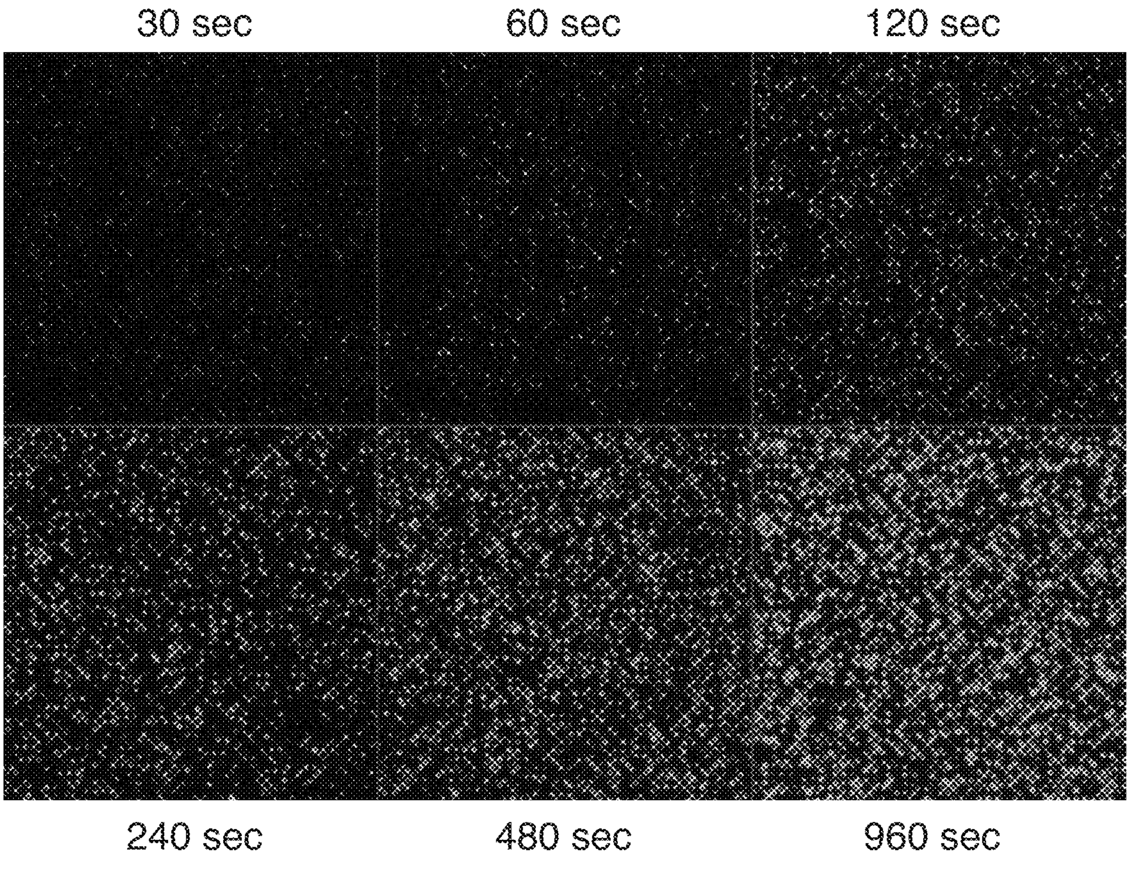
FIG. 3B. An image of clusters formed with increasing eRCA times on a patterned polymer substrate.

The following protocol is a preferred method for amplifying single template nucleic acid molecules on a solid-phase support. Circular DNA molecules (300-600 nucleotides long), were hybridized in Tris HCl buffer with NaCl to a solid support (e.g., a flow cell) that contains forward and reverse nucleic acid primers (20 to 25 nucleotides long). The primers were phosphorothioated primers. The library of circular DNA molecules (approximately 1 pM concentration) was incubated for 15-30 min at 45° C. To initiate exponential rolling circle amplification (eRCA) and after washing away excess unbound template molecules, a phi29 enzyme (or a thermostable phi29 mutant) was incubated at temperatures of 37° C. to 45° C. for 30 sec to 10 min (our experiments tested amplification times ranging from 30 seconds to 16 minutes; all of which produced clusters, as shown in FIGS. 3A and 3B).

After the circular template molecules have undergone rolling circle amplification (e.g., exponential RCA or traditional RCA), a buffer exchange occurred to remove the phi29 polymerase. This was followed by introduction of a second DNA polymerase for performing thermal bridge PCR (t-bPCR). A thermostable polymerase (e.g., Phusion) was introduced in a buffer containing dNTPs and 20% ethylene glycol as an additive. After an initial denaturation at 85° C. for 5-10 min, the solution was thermally cycled between 85° C. for 30 sec for denaturation and 1 min annealing/extension at 65° C. After 30 to 45 thermal cycles, the polymerase was removed from the flow cell via another buffer exchange. At this stage, the cluster amplification process was complete.

The monoclonal clusters can proceed to any necessary post-processing steps such as blocking of free 3' ends, removal of select amplicons, or hybridization of a sequencing primer. The clusters were quantified by introducing a nucleic acid stain (e.g., SYBR® Gold stain available from Thermo Fisher, Catalog #S11494 or a FAM (6-fluorescein amidite) labeled oligonucleotide) in the presence of a buffer, and allowed to incubate with the amplicons for 10 minutes. After a wash, the substrate containing the stained amplicons was imaged and subjected to post-processing analysis to determine cluster size and brightness. After these steps, clusters were ready for sequencing in a sequencing-by-synthesis system.

Figure 4A:
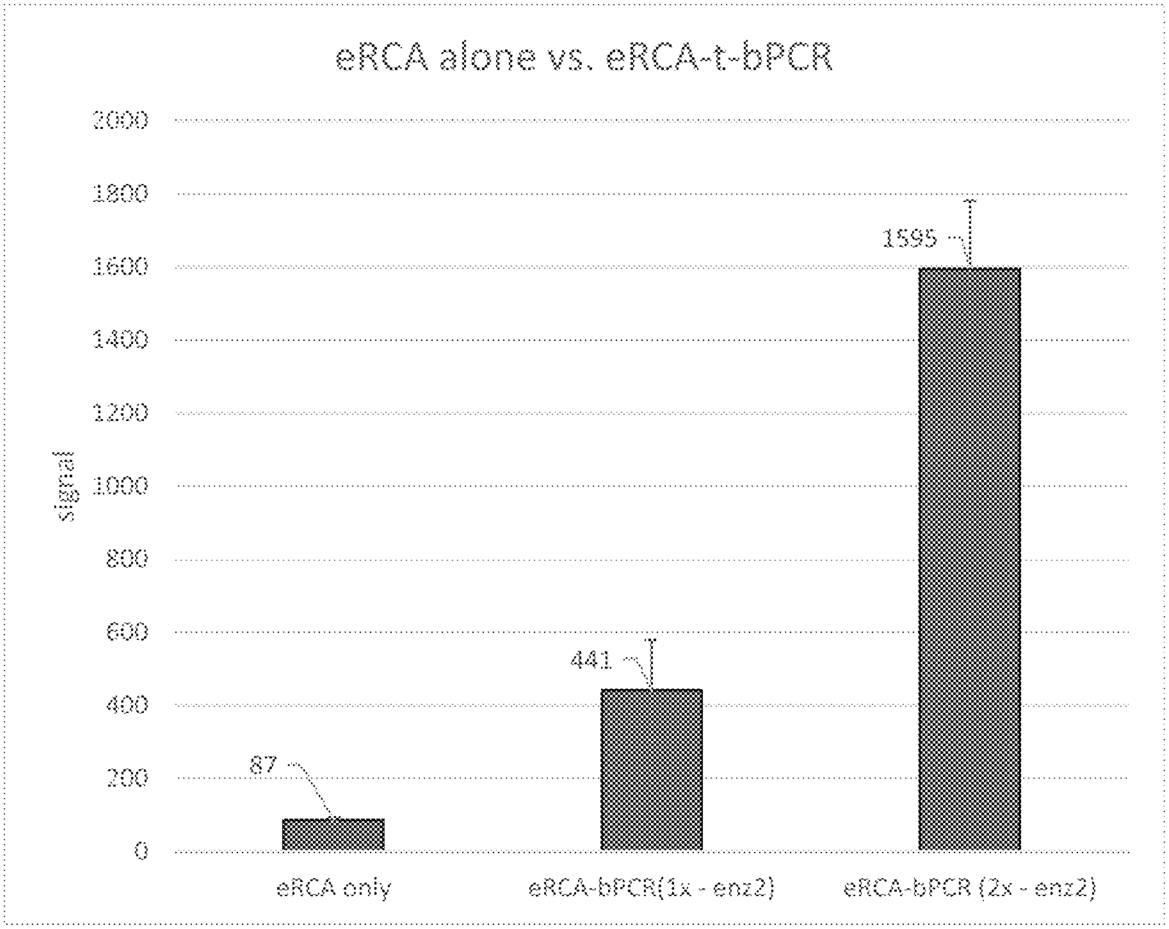
FIG. 4A. A graph highlighting how clusters formed through the amplification techniques described herein (hybrid amplification (eRCA-t-bPCR)) were approximately 5-20× brighter than eRCA alone control, depending on the concentration of polymerase used during thermal bridge PCR (t-bPCR).
Figure 4B:
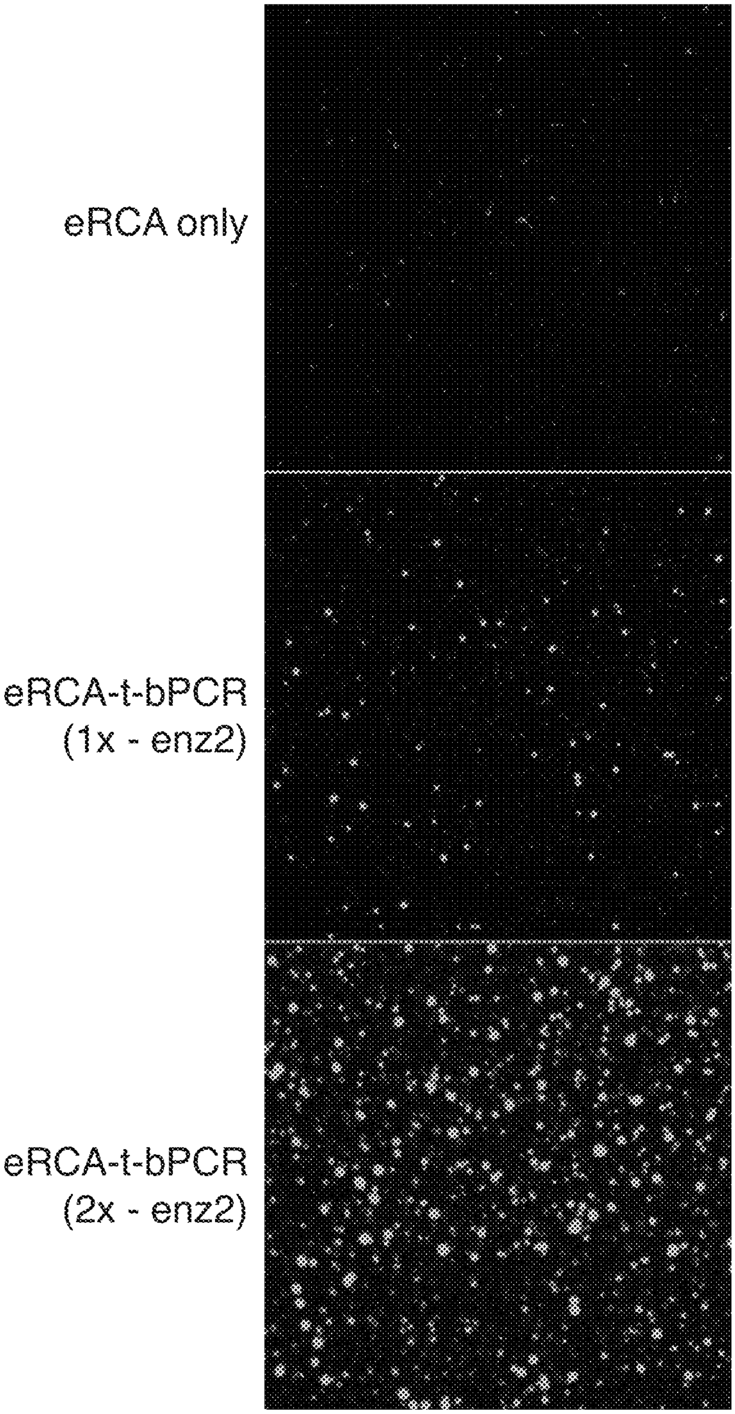
FIG. 4B. An image of clusters formed with hybrid amplification (two concentrations of polymerase shown: 1× and 2×) compared to the eRCA alone control.

Following these procedures produced fluorescent signals approximately 5-20× brighter than control clusters (i.e., clusters formed via traditional RCA); see for example FIGS. 4A and 4B comparing different amplification methods. Using these hybrid-generated clusters in a sequencing-by-synthesis device, whereby a fluorescent signal is detected upon nucleotide incorporation, the signal intensity is significantly brighter compared to sequencing results from control clusters (e.g., eRCA-generated clusters).

Example 2. Tuning Parameters to Control Amplification

Cycle Time and Temperature protocols in thermal amplification. Thermal amplification relies on thermal cycles, including i) a denaturation step (i.e., the reaction temperature is set such that the double-stranded DNA template breaks hydrogen bonds between complementary bases, yielding two single-stranded DNA molecules); ii) an annealing step (i.e., the reaction temperature is set such that the primers are annealed to each of the single-stranded DNA templates); and an extension step. The extension step is at a temperature to allow the DNA polymerase to synthesize a new DNA strand complementary to the DNA template strand by adding free dNTPs from the reaction mixture that are complementary to the template in the 5'-to-3' direction, via a condensation reaction involving the 5'-phosphate group of the dNTPs with the 3'-hydroxyl group at the end of the nascent (elongating) DNA strand. In some cases, the extension step proceeds directly upon primer hybridization without a change in conditions (e.g., at the same temperature and without adding or removing reagents).

It is beneficial to determine an appropriate temperature for the different cycles because efficiency and specificity are strongly affected by the temperature. For example, the annealing temperature should be low enough to allow for hybridization of the primer to the strand, yet high enough for the hybridization to be specific, such that the primer binds only to an exact complementary portion of the strand.

In a typical PCR, temperature cycling enables denaturing of amplicons by heat, followed by cooling to a temperature that allows hybridization of amplicons to priming regions from which a polymerase can make additional copies of the amplicons prior to the next step of thermal denaturation, which resets the cycle. In certain circumstances it is preferable to chemically assist denaturation by using additives. This is especially useful for nucleic acid libraries of a predetermined size, such as libraries used in next-generation sequencing (NGS) technologies.

Typical denaturing temperatures are around 95° C., however increasing the temperature of an aqueous system to near its boiling point puts a lot of strain on an instrument, and in the context of sequencing devices, such elevated temperature increases the potential for increased bubble formation. In such devices, and other related microfluidic devices or environments, bubbles can have adverse effect on imaging, image processing, or other chemical and physical operations. Through the use of additives, it is possible to lower the denaturing temperature (e.g., 80-85° C.). Such additives are known in the art and include ficoll, polyvinylpyrrolidone (PVT), heparin, dextran sulfate, bovine serum albumin (BSA), glycerol, 1,3-propanediol, propylene glycol, diethylene glycol, formamide, dimethylformamide, betaine (carboxymethyltrimethylammonium), DMSO, and ethylene glycol. Care should be exercised with the type and quantity of additive, as certain enzymes may not be compatible with particular additives. A series of experiments were performed and discovered the amplification methods described herein are compatible with at least betaine (carboxymethyltrimethylammonium), DMSO, and ethylene glycol.

Figure 5:
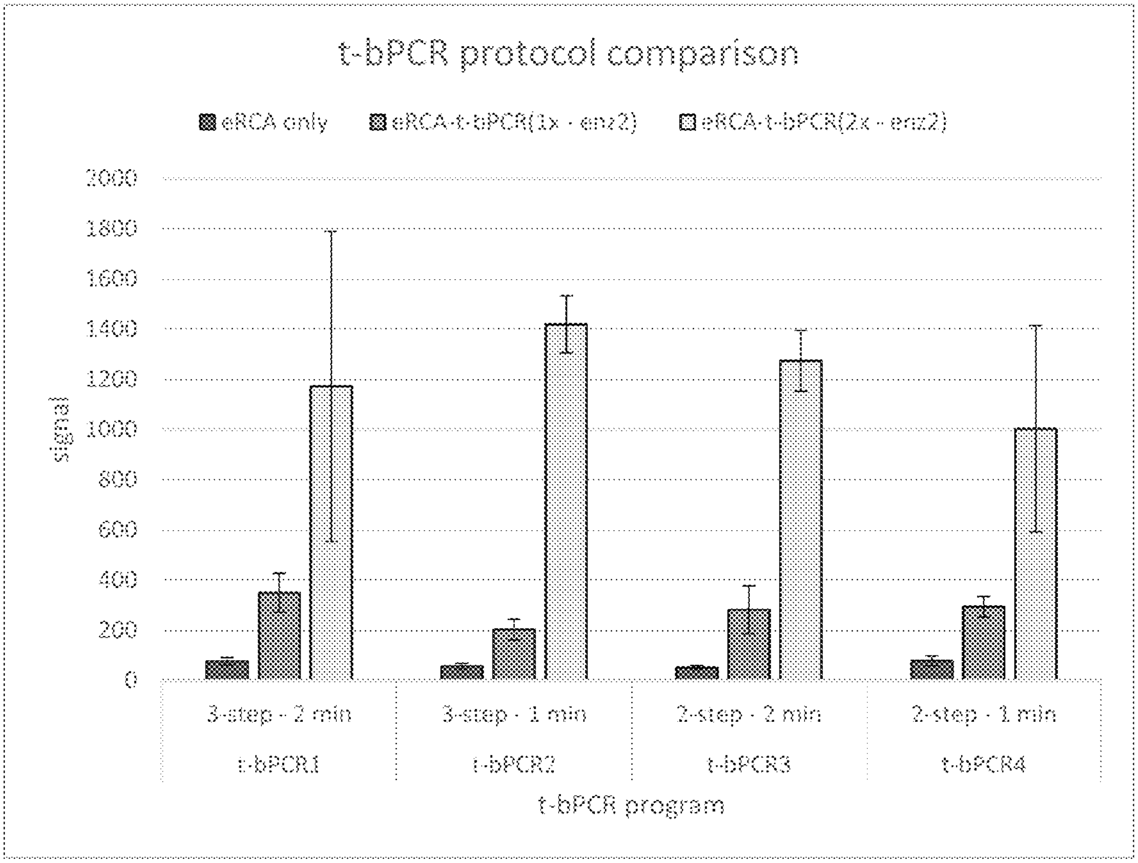
FIG. 5. A graph showing cluster brightness of hybrid amplification clusters formed using different t-bPCR programs. Both 3-step (85° C.: denature, 55° C.: anneal, 65° C.: extension) and 2-step (85° C.: denature, 65° C.: extension) programs with two different extension times (2 min and 1 min) were explored. Clusters of comparable brightness can be formed in reduced time compared to the initial t-bPCR program used.

Multiple different protocols for managing amplification were explored, see Table 1. For example, our initial protocol (t-bPCR1) utilized a 3-step thermal amplification program: (85° C.: denature for 30 seconds, 55° C.: anneal cycle for 30 seconds, 65° C.: extension cycle for 2 minutes); while an alternate protocol (t-bPCR4) is two steps: (85° C.: denature for 30 seconds, 65° C.: extension cycle for 1 minute). The hybrid amplification approach resulted in brighter signal relative to eRCA alone (i.e., the control) for all protocols explored, with protocol 4 showing similar signal to protocol 1, in a fraction of the time (FIG. 5).

TABLE 1

Non-limiting Example Amplification Protocols.

| Ref No. | Denaturation cycle | Anneal cycle | Extension cycle |
|---|---|---|---|
| t-bPCR1 | 85° C. for 30 sec | 55° C. for 30 sec | 65° C. for 2 min |
| t-bPCR2 | 85° C. for 15 sec | — | 65° C. for 1 min |
| t-bPCR3 | 85° C. for 30 sec | — | 61° C. for 1 min |
| t-bPCR4 | 85° C. for 30 sec | — | 65° C. for 1 min |
| t-bPCR5 | 85° C. for 15 sec | — | 61° C. for 1 min |
| t-bPCR6 | 85° C. for 15 sec | — | 55° C. for 1 min |

Translating the preferable solution phase PCR conditions to solid phase PCR are met with limitations such as the inefficiency of hybridizing DNA primers to amplicons, which is a crucial step for making additional amplicons. When performing temperature cycling on a solid-phase, the spatial proximity of amplicons to their reverse complement strands and the limited mobility of DNA primers favors the reannealing of full-length complementary strands as opposed to primer annealing. This stands in contrast with solution-phase PCR with unbound DNA primers, where the plurality of primer concentrations are much higher than the initial template concentration and solution-phase kinetics and diffusion shift the reaction equilibrium in favor of annealing of primers to amplicons and disfavor reannealing of full-length complementary strands.

Primer concentration. Controlling the amount of surface bound primers influences the overall density (and thus brightness) of the amplified cluster. In theory, one would want to maximize the number of surface bound primers within a confined space as a means for increasing the density (assuming one amplicon per surface bound primer). Standard surface primer concentration is around 1-25 uM total surface primer.

The parameters described herein are intertwined, raising one parameter may modify a second parameter. For example there is a balance between primer concentration and cycle time. The initial experiments started with 1.0 uM total surface primer, which produced bright clusters with the hybrid amplification methods with a longer eRCA cycle (e.g., 7.5 min). When reducing the eRCA cycle time to 30 seconds, we found that increasing the total primer concentration to 4.0 uM produced brighter clusters than 1.0 uM total primers.

Note, the primer composition should be taken into account depending on the enzyme used and whether it has exonuclease activity. For example, if an enzyme which has exonuclease activity is used to extend the primers, phosphorothioated primers are preferable. If non-phosphorothioated primers are used in the presence of an enzyme with exonuclease activity, clusters may not form.

Buffers. Reaction buffers can influence the enzyme amplification activity by containing different additives (e.g., glycerol, salts, detergents, and polymers) at various concentrations. Multiple buffers were explored, such as buffer_1: Phusion® High-Fidelity DNA Polymerase buffer (Catalog #B0518S available from New England BioLabs) and buffer_2: Phusion® GC buffer (Catalog #B0519S from New England BioLabs) for the second amplification phase (e.g., t-bPCR), as well as buffer_3: EquiPhi29™ DNA Polymerase Reaction Buffer (Catalog #B39 from Thermo Fisher), buffer_4: Reaction Buffer for phi29 DNA Polymerase (10×) (Catalog #B62 from Thermo Fisher), custom developed Tris buffers (buffer_XTris), and custom developed borate buffers (buffer_Xborate). It was found that the hybrid amplification method as described herein is compatible in all buffers. And it was also determined buffer_3 to have superior performance when using EquiPhi.

Figure 6:
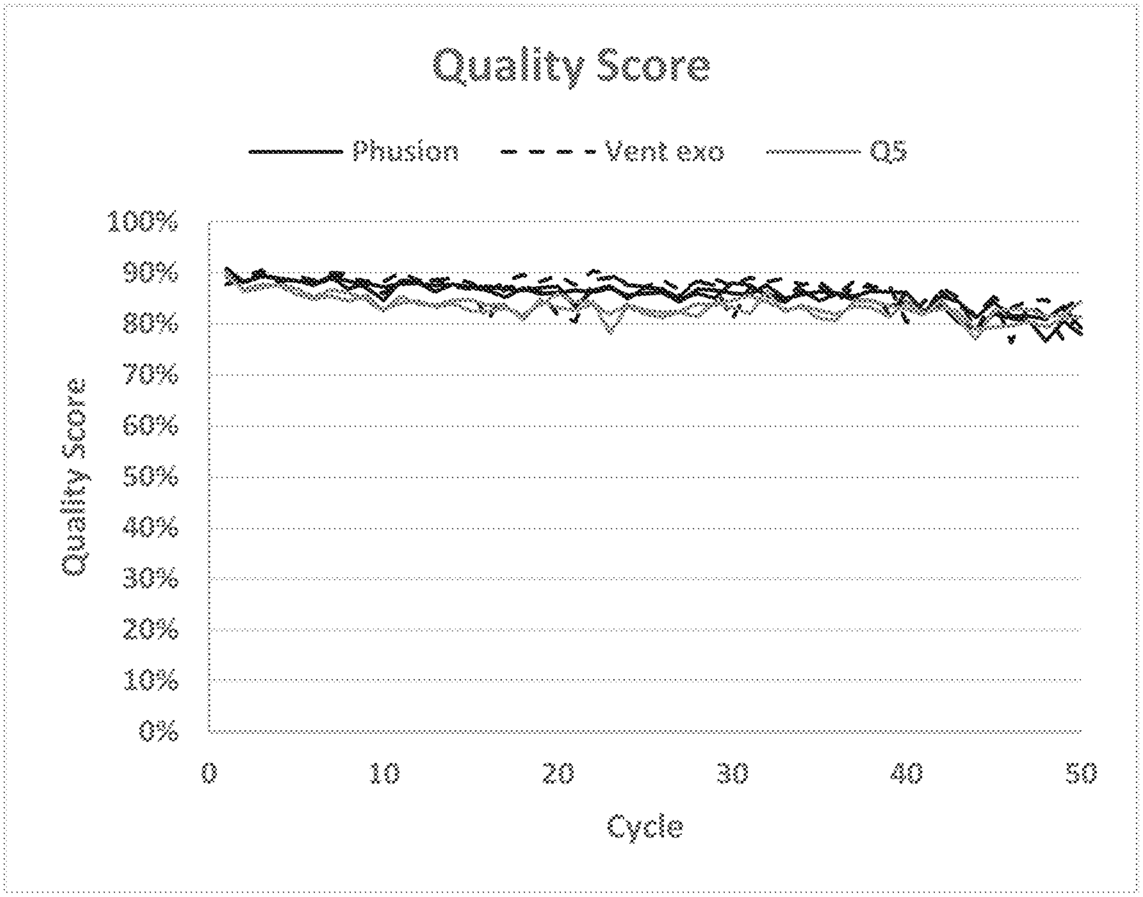
FIG. 6. A graph showing sequencing quality scores of hybrid amplification clusters produced from 3 different enzymes in the t-bPCR step: Phusion, Vent exo-, and Q5. Data from a 50-base sequence run demonstrates that multiple thermostable polymerases are compatible with hybrid amplification methods of the present disclosure, and can achieve similar sequencing quality.

Enzyme composition. The thermal bridge amplification methods described herein are compatible with a range of thermostable polymerase enzymes, such as enz1: Vent® (exo-) DNA Polymerase (Catalog #M0257S available from New England BioLabs), enz2: Phusion® High-Fidelity DNA Polymerase (Catalog #M0530S available from New England BioLabs), enz3 Q5® High-Fidelity DNA Polymerase (Catalog #M0491S), see FIG. 6. For example, when sequencing from the clusters generated with eRCA-t-bPCR, wherein the t-bPCR enzyme is enz2, the fluorescent signals start out up to 8× compared to clusters generated via eRCA alone. Even after 15 cycles of sequencing, the fluorescent signal are still 2-5 times brighter than the clusters generated from eRCA. The experiments showed there is a repeatable signal dependence that increases upon increased enz2 concentration. For example, increasing the initial concentration 10 times resulted in a 5-10-fold increase in the amount of signal compared to 1× of enz2.

Example 3. Sequencing from Clusters Generated by a Hybrid Amplifications Method

The amplification methods described herein produced clusters of oligonucleotides that allow for 2-6× more features to be detected over 50 cycles of sequencing. In an additional sequencing experiment, 120 sequencing cycles were performed with 99.9% accuracy on the PhiX genome and human exome, however comparisons to clusters generated via a single amplification method (e.g., RCA alone) were not available due to the clusters being too dim to detect and sequence upon.

Example 4. Cluster Generation eRCA-c-bPCR

The following protocol is a method for amplifying single template nucleic acid molecules on a solid-phase without thermal cycling. In thermal PCR (t-bPCR), temperature cycling enables denaturing of amplicons by heat, followed by cooling to a temperature that allows hybridization of amplicons to priming regions from which a polymerase can make additional copies of the amplicons prior to the next step of thermal denaturation, which resets the cycle. In chemical PCR (c-bPCR), the amplicons are denatured using a chemical denaturant, followed by removing the chemical denaturant to allow hybridization of the amplicons to priming regions. Such chemical denaturants are known in the art, for example formamide, guanidine, sodium salicylate, dimethyl sulfoxide (DMSO), propylene glycol, and urea may be used to denature the nucleic acids in c-bPCR cycles.

Circular DNA templates (300-600 nucleotides long), were hybridized in Tris HCl buffer with NaCl to a solid support (e.g., a flow cell) that contains forward and reverse nucleic acid primers (20 to 25 nucleotides long). The primers were cleavable primers (e.g., diol-cleavable primers). The template was extended with a mutant phi29 enzyme (e.g., EquiPhi polymerase) for 0.5 minutes, 2 minutes, or 10 minutes to generate a complement to the template. The template was removed using 0.1 M NaOH at room temperature. The extended primers were then subjected to 45 cycles of chemical bridge polymerase chain reaction (c-bPCR) using a Bst DNA Polymerase, Large Fragment (Bsf LF) for the extension step wherein solutions of 100% formamide were cycled in and out of the reaction vessel. One cycle includes extending using Bst LF in an extension mix (e.g., 1× Thermopol Buffer, dNTPs, etc.) for 60 seconds, followed by flowing in 100% formamide for 60 seconds. Note, 60 seconds of exposure was used in this experiment, but shorter times can be used. Extension and denaturation times can be at least 15 seconds each, but greater than 30 seconds is preferred. The c-PCR cycles comprise an extension step (e.g., extending using Bst LF in an extension mix (e.g., 1× Thermopol Buffer, dNTPs, etc.)) and a denaturation step (e.g., exposing the extension products to 100% formamide), and optionally a washing solution is flowed between the extension and denaturation step. The temperature of the reaction is performed at temperatures of about 40° C. to 58° C. For example, the extension occurs at 58° C., then the formamide is flowed in at 58° C. to denature. The reaction vessel is then cooled to 40° C. while in formamide. The wash buffer is then flowed in at 40° C. and the reaction vessel is heated to 58° C. prior to the next extension volume.

Figure 7A:
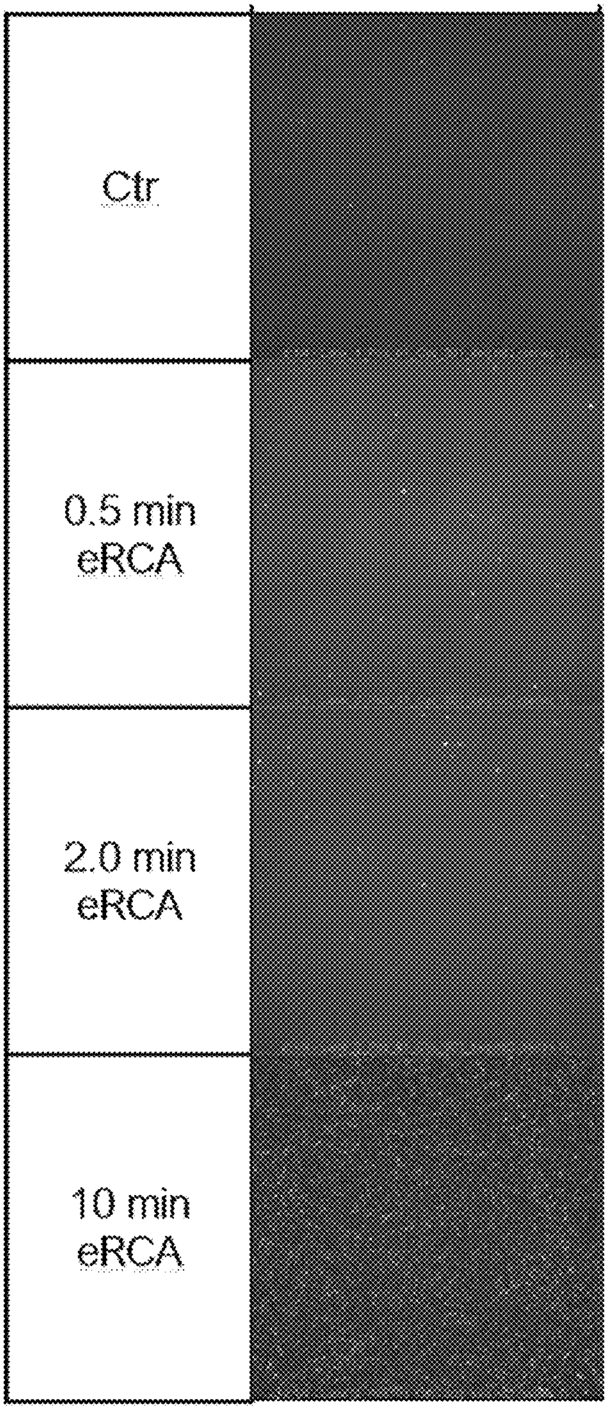
FIGS. 7A-7B. An image of the clusters produced by the eRCA-c-bPCR. The template was extended for a total of for 0.5 min, 2 min, or 10 min using exponential Rolling Circle Amplification (eRCA) method. From these extension products, performing 45 cycles of chemical-PCR produced bright clusters. The clusters generated from 10 minutes of eRCA resulted in a significant number of clusters (shown as dots in the black background). Note, the control is standard c-bPCR, no eRCA extension.
Figure 7B:
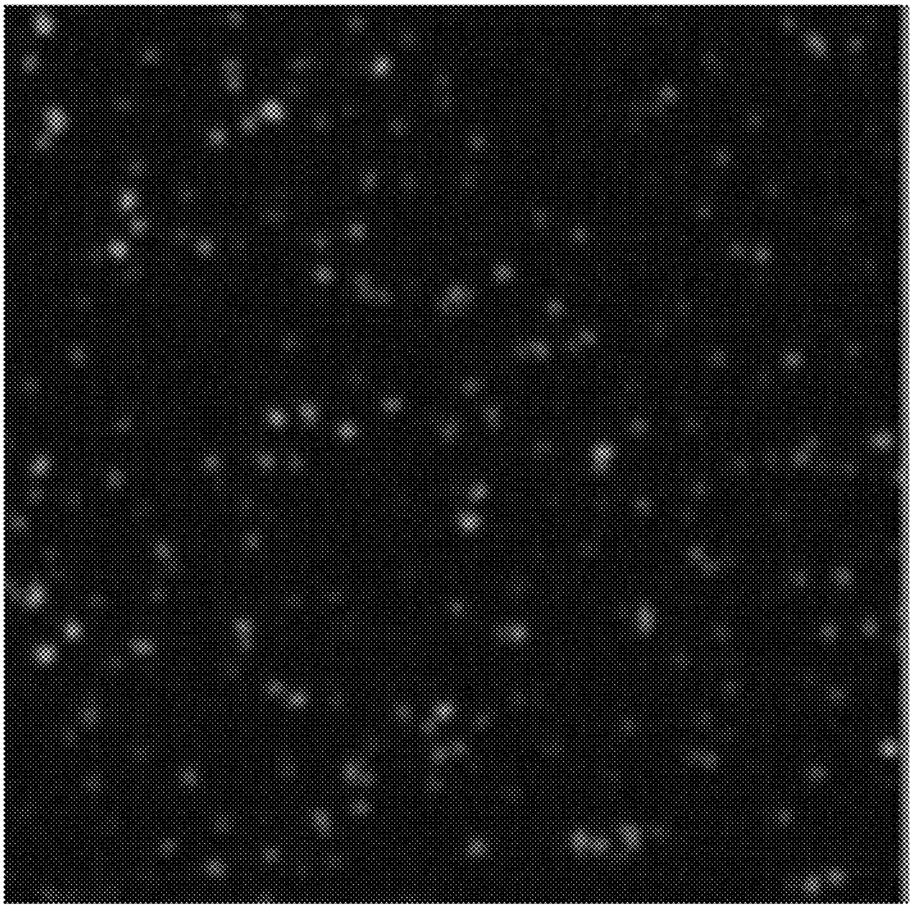

The resultant clusters were then post-processed as described elsewhere herein, e.g., the clusters are quantified by introducing a nucleic acid stain (FAM (6-fluorescein amidite) labeled oligonucleotide) in the presence of a buffer is allowed to incubate with the amplicons for 10 minutes. After a wash, the substrate containing the stained amplicons was imaged and subjected to post-processing analysis to determine cluster size and brightness. The 10 minute eRCA condition produced visible clusters of amplicons (see FIG. 7). These clusters did not show any signs of streaking. After these steps, clusters are ready for sequencing in a sequencing-by-synthesis system.

Example 5. In Situ Hybrid Amplification

The methods for hybrid amplification described herein may be applied to in situ sequencing applications. Typically, a single method of nucleic acid amplification, e.g., PCR only or RCA only, is performed in situ to generate amplicons. As described in Example 1, performing a combination of amplification techniques, for example at least one cycle of rolling circle amplification followed by at least one cycle of PCR amplification (e.g., bridge PCR with thermal or chemical denaturing) or one cycle of an isothermal amplification (e.g., loop-mediated isothermal amplification, helicase-dependent amplification, multiple displacement amplification, or RCA) method results in denser, and in the context of nucleic acid sequencing, brighter monoclonal clusters. This combination of two amplification methods (referred to herein as hybrid amplification) provides advantages compared to performing one amplification method to generate clusters of amplicons. In situ sequencing applications, an emerging area of genomics, where low amounts of target material can limit detection throughput, may therefore benefit from the increased amplification efficiency of the methods described herein. Methods for in situ spatial sequencing using, for example, padlock probes and other oligonucleotide primers to target cellular nucleic acids are known. Padlock probes are specialized ligation probes, see for example Nilsson M, et al. Science. 1994; 265(5181):2085-2088), and have been applied to detect transcribed RNA in cells, see for example Christian A T, et al. Proc Natl Acad Sci USA. 2001; 98(25):14238-14243, both of which are incorporated herein by reference in their entireties. The oligonucleotide primer is similar to a padlock probe, however with an important distinction. Typically, padlock probes hybridize to adjacent sequences and are then ligated together to form a circular oligonucleotide. Oligonucleotide primers hybridize to sequences adjacent to the target nucleic acid sequence resulting in a gap (e.g., a gap spanning the length of the target nucleic acid sequence) and are described in further detail, for example, in U.S. Pat. Application Nos. 63/140,700 and 63/140,703, both which are incorporated herein by reference in their entirety.

Briefly, cells and their surrounding milieu are attached to a substrate surface, fixed, and permeabilized. Targeted oligonucleotide primers designed for sequencing are then annealed to complementary regions which flank the nucleic acid of interest or a portion thereof. The oligonucleotide primer hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated to the second complementary region to form a circularized oligonucleotide. The resulting circularized oligonucleotide is primed with an amplification primer and extended with a strand-displacing polymerase to generate a concatemer containing multiple copies of the target nucleic acid sequence. This product is then primed and subjected to sequencing processes as described herein.

In embodiments, a polymer (e.g., a hydrogel) is added to the sample (e.g., a tissue) to provide a scaffold or matrix. In embodiments, the cell does not include an exogenous polymer. Optionally, one or more nucleotides within the amplification primer sequence, the sequencing primer sequence, and/or the immobilized oligonucleotide primer contains one or more functional moieties (e.g., bioconjugate reactive groups) that serve as attachment points to an exogenous matrix applied to the cell. In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, the complementary bioconjugate reactive groups within the cell to which the primers may be bound include one or more of lysines, cysteines, tyrosines, N- and C-termini of polypeptides, and serines. In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

After the circular template molecules have undergone rolling circle amplification (e.g., exponential RCA or traditional RCA), a solvent exchange occurs to remove the strand-displacing polymerase. This is then followed by introduction of a second DNA polymerase for performing thermal bridge PCR (t-bPCR) or chemical bridge PCR (c-bPCR). In some embodiments, c-bPCR may be more favorable than t-bPCR for performing in situ hybrid amplification due to the smaller thermal variation window when cycling between denaturation and extension. For t-bPCR, a thermostable polymerase (e.g., Phusion) is introduced in a buffer containing dNTPs and additives (e.g., 20% ethylene glycol). After an initial denaturation, the fixed cell including the amplified template polynucleotide is thermally cycled. After 10 to 45 thermal cycles, the polymerase is removed from the cell via another solvent exchange. In the case of c-bPCR, a solution containing a strand-displacement polymerase (for example, Bst LF or Bsu polymerase) is introduced to the rolling circle amplification products in the cell, followed by an incubation at 40° C.-65° C. for 0.5-2 min. This is followed by flowing a chemical denaturant, such as formamide or ethylene glycol, over the cell. After denaturation with the chemical denaturant, the cycle is reset by a wash step and flowing the strand-displacement polymerase over the cell. This cycle can be repeated 10 to 45 times in consecutive c-bPCR cycles.

The monoclonal clusters can proceed to any necessary post-processing steps such as blocking of free 3' ends, removal of select amplicons, or hybridization of a sequencing primer. The clusters may be quantified by introducing a nucleic acid stain (e.g., SYBR® Gold stain available from Thermo Fisher, Catalog #S11494 or a FAM (6-fluorescein amidite) labeled oligonucleotide) in the presence of a buffer and allowed to incubate with the amplicons. After a wash, the cells containing the stained amplicons are imaged and subjected to post-processing analysis to determine cluster size and brightness. After these steps, clusters are ready for in situ sequencing in an in situ sequencing system.

These amplicons may be used for alternative sequencing technologies that have been described based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization), FISSEQ (fluorescent in situ sequencing), and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; Lee J H et al. Nat. Protoc. 2015; 10(3):442-58); and Sansone, A. Nat Methods 16, 458; 2019). Some of these techniques have been combined with super-resolution microscopy, expansion microscopy, or both, to increase the resolution and allow more transcripts to be resolved and thus counted.

In embodiments, sequencing includes encoding the sequencing read into a codeword. Useful encoding schemes include those developed for telecommunications, coding theory and information theory such as those set forth in Hamming, *Coding and Information Theory, $2^{nd}$ Ed.* Prentice Hall, Englewood Cliffs, N.J. (1986) and Moon T K. Error Correction Coding: Mathematical Methods and Algorithms. ed. 1st Wiley: 2005., each of which are incorporated herein by reference. A useful encoding scheme uses a Hamming code. A Hamming code can provide for signal (and therefore sequencing and barcode) distinction. In this scheme, signal states detected from a series of nucleotide incorporation and detection events (i.e., while sequencing the oligonucleotide barcode) can be represented as a series of the digits to form a codeword, the codeword having a length equivalent to the number incorporation/detection events. The digits can be binary (e.g. having a value of 1 for presence of signal and a value of 0 for absence of the signal) or digits can have a higher radix (e.g., a ternary digit having a value of 1 for fluorescence at a first wavelength, a value of 2 for fluorescence at a second wavelength, and a value of 0 for no fluorescence at those wavelengths, etc.). Barcode discrimination capabilities are provided when codewords can be quantified via Hamming distances between two codewords (i.e., barcode 1 having codeword 1, and barcode 2 having codeword 2, etc.).

In embodiments, the barcodes in the known set of barcodes have a specified Hamming distance. In embodiments, the Hamming distance is 4 to 15. In embodiments, the Hamming distance is 8 to 12. In embodiments, the Hamming distance is 10. In embodiments, the Hamming distance is 0 to 100. In embodiments, the Hamming distance is 0 to 15. In embodiments, the Hamming distance is 0 to 10. In embodiments, the Hamming distance is 1 to 10. In embodiments, the Hamming distance is 5 to 10. In embodiments, the Hamming distance is 1 to 100.

Following these procedures may produce fluorescent signals approximately 5-20× brighter than control clusters (i.e., clusters formed via traditional RCA). Using these hybrid-generated clusters in a sequencing-by-synthesis device, whereby a fluorescent signal is detected upon nucleotide incorporation, the signal intensity may be significantly brighter compared to sequencing results from control clusters (e.g., eRCA-only generated clusters).

P-Embodiments

The present disclosure provides the following illustrative embodiments.

Embodiment P1. A method of amplifying a polynucleotide for sequencing comprising: (a) amplifying a template polynucleotide by extending an amplification primer with a strand-displacing polymerase, wherein the template polynucleotide comprises a continuous strand lacking free 5' and 3' ends, and wherein the primer extension generates a first extension product comprising multiple complements of the template polynucleotide; (b) amplifying the first extension product or a complement thereof on a solid support comprising a plurality of primers attached to said solid support, wherein the plurality of primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment P2. The method of embodiment P1, wherein wherein step (b) comprises (i) extension of a 3' end of a first substrate-bound primer extension product hybridized to a second substrate-bound primer extension product, and/or (ii) extension of a 3' end of a third substrate-bound primer extension product hybridized to itself.

Embodiment P3. The method of embodiment P1 or embodiment P2, wherein the amplification primer is attached to the solid support.

Embodiment P4. The method of embodiment P1 or embodiment P2, wherein the amplification primer is in solution.

Embodiment P5. The method of embodiment P1 or embodiment P2, wherein the template polynucleotide comprises single-stranded circular DNA.

Embodiment P6. The method of embodiment P1 or embodiment P2, wherein the template polynucleotide comprises double-stranded DNA.

Embodiment P7. The method of embodiment P1, further comprising forming the template polynucleotide by ligating ends of a linear polynucleotide together.

Embodiment P8. The method of embodiment P1, further comprising forming the template polynucleotide by ligating a hairpin adapter to an end of a linear polynucleotide.

Embodiment P9. The method of embodiment P8, wherein forming the template polynucleotide comprises ligating hairpin adapters to both ends of the linear polynucleotide.

Embodiment P10. The method of any one of embodiment P1 to embodiment P9, wherein step (a) comprises exponential rolling circle amplification (eRCA).

Embodiment P11. The method of any one of embodiment P1 to embodiment P9, wherein step (a) comprises hyberbranched rolling circle amplification (HRCA).

Embodiment P12. The method of any one of embodiment P1 to embodiment P11, wherein the amplification primer comprises one or more phosphorothioate nucleotides.

Embodiment P13. The method of any one of embodiment P1 to embodiment P12, wherein the step of extending the amplification primer comprises incubation with the strand-displacing polymerase (a) for about 10 seconds to about 30 minutes, and/or (b) at a temperature of about 20° C. to about 50° C.

Embodiment P14. The method of embodiment P13, wherein incubation with the strand-displacing polymerase is for about 0.5 minutes to about 16 minutes.

Embodiment P15. The method of embodiment P14, wherein incubation with the strand-displacing polymerase is for about 0.5 minutes to about 10 minutes.

Embodiment P16. The method of embodiment P14, wherein incubation with the strand-displacing polymerase is for about 1 minute to about 5 minutes.

Embodiment P17. The method of any one of embodiment P13 to embodiment P16, wherein incubation with the strand-displacing polymerase is at a temperature of about 35° C. to 42° C.

Embodiment P18. The method of any one of embodiment P13 to embodiment P16, wherein incubation with the strand-displacing polymerase is at a temperature of about 37° C. to 40° C.

Embodiment P19. The method of any one of embodiment P1 to embodiment P18, wherein the strand-displacing polymerase is phi29 polymerase, phi29 mutant polymerase or a thermostable phi29 mutant polymerase.

Embodiment P20. The method of any one of embodiment P1 to embodiment P19, wherein the strand-displacing polymerase is removed or inactivated prior to step (b).

Embodiment P21. The method of any one of embodiment P1 to embodiment P20, wherein step (b) comprises addition of a second polymerase.

Embodiment P22. The method of any one of embodiment P1 to embodiment P21, wherein step (b) comprises thermal bridge polymerase chain reaction amplification.

Embodiment P23. The method of embodiment P22, wherein step (b) comprises incubation in an additive that lowers a DNA denaturation temperature.

Embodiment P24. The method of embodiment P23, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment P25. The method of any one of embodiment P1 to embodiment P24, wherein the plurality of cycles is about 10 to about 45 cycles.

Embodiment P26. The method of any one of embodiment P1 to embodiment P24, wherein the plurality of cycles is about 20 to about 30 cycles.

Embodiment P27. The method of any one of embodiment P1 to embodiment P26, wherein step (b) comprising an initial denaturation at about 85° C.-95° C. for about 1 minute to about 10 minutes.

Embodiment P28. The method of any one of embodiment P1 to embodiment P26, wherein step (b) comprising an initial denaturation at about 85° C.-95° C. for about 5 minutes to about 10 minutes.

Embodiment P29. The method of any one of embodiment P1 to embodiment P28, wherein the plurality of cycles comprises thermally cycling between (i) about 85° C. for about 15-30 sec for denaturation, and (ii) about 65° C. for about 1 minute for annealing/extension of the primer.

Embodiment P30. The method of any one of embodiment P1 to embodiment P28, wherein the plurality of cycles comprises thermally cycling between (i) about 85° C. for about 15-30 sec for denaturation, and (ii) about 65° C. for about 30 seconds for annealing/extension of the primer.

Embodiment P31. The method of any one of embodiment P1 to embodiment P30, wherein step (b) comprises denaturation using a chemical denaturant.

Embodiment P32. The method of any one of embodiment P1 to embodiment P31, wherein step (b) comprises denaturation using acetic acid, hydrochloric acid, nitric acid, formamide, guanidine, sodium salicylate, sodium hydroxide, dimethyl sulfoxide (DMSO), propylene glycol, urea, or a mixture thereof.

Embodiment P33. The method of any one of embodiment P1 to embodiment P32, wherein the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment P34. The method of embodiment P33, wherein the circular polynucleotide is about 300 to about 600 nucleotides in length.

Embodiment P35. The method of any one of embodiment P1 to embodiment P34, further comprising sequencing the amplification products of step (b).

Embodiment P36. A composition comprising: (a) a first extension product comprising multiple complements of a template polynucleotide; and (b) a solid support comprising a plurality primers attached to said solid support, wherein the plurality of primers comprise a plurality of forward primers with complementarity to the first extension product and a plurality of reverse primers with complementarity to a complement of the first extension product.

Embodiment P37. The composition of embodiment P36, further comprising a polymerase.

Embodiment P38. The composition of embodiment P37, wherein the polymerase is a strand-displacing polymerase.

Embodiment P39. The composition of embodiment P38, wherein the strand-displacing polymerase is phi29 polymerase, phi29 mutant polymerase or a thermostable phi29 mutant polymerase.

Embodiment P40. The composition of any one of embodiment P36 to embodiment P39, further comprising an additive that lowers a DNA denaturation temperature.

Embodiment P41. The composition of embodiment P40, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment P42. The composition of any one of embodiment P36 to embodiment P41, further comprising a denaturant.

Embodiment P43. The composition of embodiment P42, wherein the denaturant is acetic acid, hydrochloric acid, nitric acid, formamide, guanidine, sodium salicylate, sodium hydroxide, dimethyl sulfoxide (DMSO), propylene glycol, urea, or a mixture thereof.

Embodiment P44. The composition of any one of embodiment P36 to embodiment P43, wherein the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment P45. The composition of embodiment P44, wherein the circular polynucleotide is about 300 to about 600 nucleotides in length.

Embodiment P46. The composition of embodiment P36, wherein the template polynucleotide comprises one or more adapters.

Embodiment P47. The composition of embodiment P46, wherein the adapter comprises a hairpin loop structure.

Embodiment P48. A kit comprising a composition according to any one of embodiment P36 to embodiment P47.

Additional Embodiments

The present disclosure provides the following additional illustrative embodiments.

Embodiment 1. A method of amplifying a polynucleotide for sequencing comprising: (a) amplifying a template polynucleotide by extending an amplification primer with a strand-displacing polymerase, wherein the template polynucleotide comprises a continuous strand lacking free 5' and 3' ends, and wherein the primer extension generates a first extension product comprising multiple complements of the template polynucleotide; (b) amplifying the first extension product or a complement thereof on a solid support comprising a plurality of primers attached to said solid support, wherein the plurality of primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment 2. The method of embodiment 1, wherein step (b) comprises (i) extension of a 3' end of a first substrate-bound primer extension product hybridized to a second substrate-bound primer extension product, and/or (ii) extension of a 3' end of a third substrate-bound primer extension product hybridized to itself.

Embodiment 3. The method of embodiments 1 or 2, wherein the amplification primer is attached to the solid support.

Embodiment 4. A method of amplifying a polynucleotide of a cell in situ for sequencing comprising: (a) amplifying a template polynucleotide by extending an amplification primer with a strand-displacing polymerase, wherein the template polynucleotide comprises a continuous strand lacking free 5' and 3' ends, and wherein the primer extension generates a first extension product comprising multiple complements of the template polynucleotide; (b) amplifying the first extension product or a complement thereof in a cell, said cell comprising a plurality of immobilized primers, wherein the plurality of immobilized primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment 5. The method of embodiment 4, wherein step (b) comprises (i) extension of a 3' end of a first immobilized primer extension product hybridized to a second immobilized primer extension product, and/or (ii) extension of a 3' end of an immobilized primer extension product hybridized to itself.

Embodiment 6. The method of embodiments 4 or 5, wherein the amplification primer comprises a first bioconjugate reactive group.

Embodiment 7. The method of any one of embodiments 4-6, wherein the amplification primer is attached to a cellular component.

Embodiment 8. The method of embodiment 7, wherein the cellular component comprises a second bioconjugate reactive group.

Embodiment 9. The method of embodiment 8, wherein the first bioconjugate reactive group is attached to the second bioconjugate reactive group by covalent or non-covalent bonding.

Embodiment 10. The method of embodiments 4 or 5, wherein the cell further comprises an exogenous polymer or exogenous hydrogel.

Embodiment 11. The method of embodiment 10, wherein the plurality of immobilized primers is bound to the exogenous polymer or exogenous hydrogel.

Embodiment 12. The method of embodiment 10, wherein the immobilized primer extension product is bound to the exogenous polymer or exogenous hydrogel.

Embodiment 13. The method of any one of embodiments 4-12, wherein the cell forms part of a tissue in situ.

Embodiment 14. The method of any one of embodiments 4-12, wherein the cell is a prokaryotic cell.

Embodiment 15. The method of any one of embodiments 4-12, wherein the cell is a eukaryotic cell.

Embodiment 16. The method of any one of embodiments 4-15, wherein the cell is permeabilized and immobilized to a solid support.

Embodiment 17. The method of any one of embodiments 1-3, wherein the amplification primer is in solution.

Embodiment 18. The method of any one of embodiments 1-16, wherein the template polynucleotide comprises single-stranded circular DNA.

Embodiment 19. The method of any one of embodiments 1-16, wherein the template polynucleotide comprises double-stranded DNA.

Embodiment 20. The method of any one of embodiments 4-16, wherein the template polynucleotide comprises RNA.

Embodiment 21. The method of embodiments 1 or 4, further comprising forming the template polynucleotide by ligating ends of a linear polynucleotide together.

Embodiment 22. The method of embodiments 1 or 4, further comprising forming the template polynucleotide by ligating a hairpin adapter to an end of a linear polynucleotide.

Embodiment 23. The method of embodiment 22, wherein forming the template polynucleotide comprises ligating hairpin adapters to both ends of the linear polynucleotide.

Embodiment 24. The method of any one of embodiments 1-23, wherein step (a) comprises rolling circle amplification (RCA).

Embodiment 25. The method of any one of embodiments 1-23, wherein step (a) comprises exponential rolling circle amplification (eRCA).

Embodiment 26. The method of any one of embodiments 1-23, wherein step (a) comprises hyperbranched rolling circle amplification (HRCA).

Embodiment 27. The method of any one of embodiments 1-26, wherein the amplification primer comprises one or more phosphorothioate nucleotides.

Embodiment 28. The method of any one of embodiments 1-27, wherein the step of extending the amplification primer comprises incubation with the strand-displacing polymerase (a) for about 10 seconds to about 30 minutes, and/or (b) at a temperature of about 20° C. to about 50° C.

Embodiment 29. The method of embodiment 28, wherein incubation with the strand-displacing polymerase is for about 0.5 minutes to about 16 minutes.

Embodiment 30. The method of embodiment 28, wherein incubation with the strand-displacing polymerase is for about 0.5 minutes to about 10 minutes.

Embodiment 31. The method of embodiment 28, wherein incubation with the strand-displacing polymerase is for about 1 minute to about 5 minutes.

Embodiment 32. The method of any one of embodiments 28-31, wherein incubation with the strand-displacing polymerase is at a temperature of about 35° C. to 42° C.

Embodiment 33. The method of any one of embodiments 28-31, wherein incubation with the strand-displacing polymerase is at a temperature of about 37° C. to 40° C.

Embodiment 34. The method of any one of embodiments 1-33, wherein the strand-displacing polymerase is phi29 polymerase, phi29 mutant polymerase or a thermostable phi29 mutant polymerase.

Embodiment 35. The method of any one of embodiments 1-34, wherein the strand-displacing polymerase is removed or inactivated prior to step (b).

Embodiment 36. The method of any of embodiments 1-35, wherein step (b) comprises addition of a second polymerase.

Embodiment 37. The method of any one of embodiments 1-36, wherein step (b) comprises thermal bridge polymerase chain reaction amplification.

Embodiment 38. The method of embodiment 37, wherein step (b) comprises incubation in an additive that lowers a DNA denaturation temperature.

Embodiment 39. The method of embodiment 38, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment 40. The method of any one of embodiments 1-39, wherein the plurality of cycles is about 10 to about 45 cycles.

Embodiment 41. The method of any one of embodiments 1-39, wherein the plurality of cycles is about 20 to about 30 cycles.

Embodiment 42. The method of any one of embodiments 1-41, wherein step (b) comprising an initial denaturation at about 85° C.-95° C. for about 1 minute to about 10 minutes.

Embodiment 43. The method of any one of embodiments 1-41, wherein step (b) comprising an initial denaturation at about 85° C.-95° C. for about 5 minutes to about 10 minutes.

Embodiment 44. The method of any one of embodiments 1-43, wherein the plurality of cycles comprises thermally cycling between (i) about 85° C. for about 15-30 sec for denaturation, and (ii) about 65° C. for about 1 minute for annealing/extension of the primer.

Embodiment 45. The method of any one of embodiments 1-43, wherein the plurality of cycles comprises thermally cycling between (i) about 85° C. for about 15-30 sec for denaturation, and (ii) about 65° C. for about 30 seconds for annealing/extension of the primer.

Embodiment 46. The method of any one of embodiments 1-45, wherein step (b) comprises denaturation using a chemical denaturant.

Embodiment 47. The method of any one of embodiments 1-46, wherein amplifying the first extension product comprises a plurality of fluidic cycles of strand denaturation using a chemical denaturant, and a plurality of fluidic cycles of primer extension comprising an extension mixture.

Embodiment 48. The method of any one of embodiments 1-47, wherein step (b) comprises denaturation using acetic acid, hydrochloric acid, nitric acid, formamide, guanidine, sodium salicylate, sodium hydroxide, dimethyl sulfoxide (DMSO), propylene glycol, urea, or a mixture thereof.

Embodiment 49. The method of any one of embodiments 1-48, wherein step (b) comprises thermally cycling between about 40° C. to about 65° C. during the plurality of fluidic cycles.

Embodiment 50. The method of any one of embodiments 1-48, wherein step (b) comprises modulating the reaction temperature prior to initiating the next cycle.

Embodiment 51. The method of embodiments 47 or 48, wherein the plurality of fluidic cycles comprises about 5 to about 45 cycles.

Embodiment 52. The method of any one of embodiments 1-50, wherein the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment 53. The method of embodiment 52, wherein the circular polynucleotide is about 300 to about 600 nucleotides in length.

Embodiment 54. The method of any one of embodiments 1-53, further comprising sequencing the amplification products of step (b).

Embodiment 55. A composition comprising: (a) a first extension product comprising multiple complements of a template polynucleotide; and (b) a solid support comprising a plurality of primers attached to said solid support, wherein the plurality of primers comprise a plurality of forward primers with complementarity to the first extension product and a plurality of reverse primers with complementarity to a complement of the first extension product.

Embodiment 56. A composition comprising: (a) a first in situ extension product comprising multiple complements of a template polynucleotide; and (b) a cell comprising a plurality of immobilized primers, wherein the plurality of immobilized primers comprise a plurality of forward primers with complementarity to the first in situ extension product and a plurality of reverse primers with complementarity to a complement of the first in situ extension product.

Embodiment 57. The composition of embodiments 55 or 56, further comprising a polymerase.

Embodiment 58. The composition of embodiment 57, wherein the polymerase is a strand-displacing polymerase.

Embodiment 59. The composition of embodiment 58, wherein the strand-displacing polymerase is phi29 polymerase, phi29 mutant polymerase or a thermostable phi29 mutant polymerase.

Embodiment 60. The composition of any one of embodiments 55-59, further comprising an additive that lowers a DNA denaturation temperature.

Embodiment 61. The composition of embodiment 60, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment 62. The composition of any one of embodiments 55-61, further comprising a denaturant.

Embodiment 63. The composition of embodiment 62, wherein the denaturant is acetic acid, hydrochloric acid, nitric acid, formamide, guanidine, sodium salicylate, sodium hydroxide, dimethyl sulfoxide (DMSO), propylene glycol, urea, or a mixture thereof.

Embodiment 64. The composition of any one of embodiments 55-63, wherein the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment 65. The composition of embodiment 64, wherein the circular polynucleotide is about 300 to about 600 nucleotides in length.

Embodiment 66. The composition of any one of embodiments 55-65, wherein the template polynucleotide comprises one or more adapters.

Embodiment 67. The composition of embodiment 66, wherein the adapter comprises a hairpin loop structure.

Embodiment 68. A kit comprising a composition according to any one of embodiments 55-67.

What is claimed is:

1. A method of amplifying a circular template polynucleotide in situ, the method comprising:

(a) amplifying the circular template polynucleotide in a tissue section comprising a cell by extending a first amplification primer with a strand-displacing polymerase to generate a first extension product comprising one or more complements of the circular template polynucleotide, wherein extending occurs for about 30 seconds to 30 minutes; and (b) contacting the first extension product with a second amplification primer in the tissue section, wherein said second amplification primer is attached to a polymer matrix or a cellular component in or on the cell, and extending said second amplification primer with a polymerase to generate a second immobilized extension product comprising one or more complements of the first extension product in situ.

2. The method of claim 1, wherein step (b) comprises (i) extension of a 3' end of the first extension product hybridized to the second extension product, and/or (ii) extension of a 3' end of an extension product hybridized to itself.

3. The method of claim 1, wherein each amplification primer comprises at least 17 nucleotides.

4. The method of claim 1, wherein the second amplification primer is attached to the cellular component.

5. The method of claim 1, wherein the polymer matrix is an exogenous polymer matrix.

6. The method of claim 5, wherein the second amplification primer is covalently bound to the exogenous polymer matrix.

7. The method of claim 1, wherein the cell forms part of a tissue section in situ, or wherein the cell is a prokaryotic cell or a eukaryotic cell.

8. The method of claim 1, wherein the cell is permeabilized and immobilized to a solid support.

9. The method of claim 1, wherein the circular template polynucleotide comprises single-stranded circular DNA.

10. The method of claim 9, wherein the circular template polynucleotide comprises one or more ribonucleotides.

11. The method of claim 9, wherein prior to step (a), forming the circular template polynucleotide comprises ligating ends of a linear polynucleotide together.

12. The method of claim 1, wherein step (a) comprises rolling circle amplification (RCA), exponential rolling circle amplification (eRCA), or hyperbranched rolling circle amplification (HRCA).

13. The method of claim 1, wherein step (a) comprises incubation with the strand-displacing polymerase at a temperature of about 20° C. to about 50° C.

14. The method of claim 1, wherein step (b) comprises a polymerase different than the polymerase of step (a).

15. The method of claim 1, wherein the circular template polynucleotide of step (a) is about 100 to about 1000 nucleotides in length, about 100 to about 300 nucleotides in length, about 300 to about 500 nucleotides in length, or about 500 to about 1000 nucleotides in length.

16. The method of claim 1, further comprising sequencing the first immobilized extension product and the second immobilized extension product.

17. The method of claim 1, wherein prior to step (a), forming the circular template polynucleotide comprises ligating ends of a linear polynucleotide together with the aid of a bridging oligonucleotide that is complementary with the two ends of the linear polynucleotide.

18. The method of claim 1, wherein step (b) further comprises contacting the second extension product with a third amplification primer in said cell, wherein said third amplification primer is attached to a polymer matrix or a cellular component, and extending said third amplification primer with a polymerase to generate an immobilized amplification product comprising one or more complements of the second extension product.

19. The method of claim 1, wherein the circular template polynucleotide comprises the complement of an endogenous nucleic acid sequence.

20. The method of claim 1, wherein the tissue section comprises a Formalin-Fixed Paraffin-Embedded (FFPE) tissue sample.

21. The method of claim 1, wherein the tissue section comprises bone tissue.

22. The method of claim 1, wherein prior to step (a), the method comprises hybridizing a first sequence of an oligonucleotide primer to a target nucleic acid molecule and hybridizing a second sequence of the oligonucleotide primer to the target nucleic acid molecule, and ligating the first sequence and second sequence together to form the circular template polynucleotide in the tissue.

23. The method of claim 1, wherein the first extension product is covalently attached to a first protein and wherein the second extension product is covalently attached to a second protein.

* * * * *